United States Patent
Li

(10) Patent No.: US 10,647,746 B2
(45) Date of Patent: May 12, 2020

(54) ANTIBACTERIAL CYCLIC LIPOPEPTIDES

(71) Applicant: Versitech Limited, Hong Kong (HK)

(72) Inventor: Xuechen Li, Hong Kong (HK)

(73) Assignee: Versitech Limited, Hong Kong (HK)

( * ) Notice: Subject to any disclaimer, the term of this patent is extended or adjusted under 35 U.S.C. 154(b) by 0 days.

(21) Appl. No.: 15/093,950

(22) Filed: Apr. 8, 2016

(65) Prior Publication Data

US 2017/0291923 A1    Oct. 12, 2017

(51) Int. Cl.
  *C07K 7/54*   (2006.01)
  *C07K 7/08*   (2006.01)
  *A61K 38/00*  (2006.01)

(52) U.S. Cl.
  CPC .......... *C07K 7/54* (2013.01); *C07K 7/08* (2013.01); *A61K 38/00* (2013.01)

(58) Field of Classification Search
  CPC .... A61K 2300/00; A61K 38/10; A61K 38/12; A61K 38/08; A61K 38/14; A61K 45/06; C07K 7/08; C07K 1/145; C07K 5/0821; C07K 11/02; C07K 7/56
  See application file for complete search history.

(56) References Cited

U.S. PATENT DOCUMENTS

| | | |
|---|---|---|
| 4,537,717 A | 8/1985 | Abbott |
| 6,468,967 B1 | 10/2002 | Oleson, Jr. et al. |
| 6,624,143 B1 | 9/2003 | Vertesy |
| 6,852,689 B2 | 2/2005 | Oleson, Jr. et al. |
| RE39,071 E | 4/2006 | Baker et al. |
| 8,058,238 B2 | 11/2011 | Kelleher et al. |
| 8,129,342 B2 | 3/2012 | Kelleher et al. |
| 8,507,647 B2 | 8/2013 | Metcalf, III et al. |
| 8,754,040 B2 | 6/2014 | Sekimizu et al. |
| 8,835,382 B2 | 9/2014 | O'Connor et al. |
| 8,853,357 B2 | 10/2014 | Kelleher et al. |
| 9,090,667 B2 | 7/2015 | Kim et al. |
| 9,138,456 B2 | 9/2015 | O'Connor et al. |
| 9,243,036 B2 | 1/2016 | Atreya et al. |
| 9,260,481 B2 | 2/2016 | Gualtieri et al. |
| 9,283,287 B2 | 3/2016 | Chakraborty et al. |
| 9,303,079 B2 | 4/2016 | Chakraborty et al. |
| 2015/0126707 A1 | 5/2015 | Li |

FOREIGN PATENT DOCUMENTS

| | | | |
|---|---|---|---|
| GB | 2120257 A | * 11/1983 | ............... C07K 7/08 |
| WO | 1999043700 | 9/1999 | |
| WO | WO 0144274 A1 | * 6/2001 | ............... C07K 7/08 |
| WO | 2002005837 | 1/2002 | |

(Continued)

OTHER PUBLICATIONS

Muangsiri et al., Studies on the reactions between daptomycin and glyceraldehyde, International Journal of Pharmaceutics, vol. 289:133-150 (2005).*

(Continued)

*Primary Examiner* — Randall L Beane
(74) *Attorney, Agent, or Firm* — Pabst Patent Group LLP

(57) ABSTRACT

Described are design and generation of a set of novel cyclic lipopeptides as potential antibacterial agents. New daptomycin analogues are generated by chemical synthesis, which makes introduction of an unnatural amino acid and any modification into daptomycin possible.

13 Claims, 17 Drawing Sheets

Modification 2 (methylation at Kyn)

(56) References Cited

FOREIGN PATENT DOCUMENTS

| WO | 2002056829 | 7/2002 |
| WO | 2007072082 | 6/2007 |
| WO | 2012162567 | 11/2012 |

OTHER PUBLICATIONS

Mills et al., Estimating the Power of Indirect Comparisons: A Simulation Study, PLoS ONE 6(1): e16237. doi:10.1371/journal.pone.0016237 (Jan. 21, 2011) (Year: 2011).*
Song et. al., Validity of indirect comparison for estimating efficacy of competing interventions: empirical evidence from published meta-analyses, BMJ, vol. 326:1-5 (Mar. 1, 2003) (Year: 2003).*
Cucherat et al.; Summary Report: Indirect comparisons Methods and validity, HAS Department of Medecines Assessment (Jul. 2009), 66 pages (Year: 2009).*
International Search Report dated May 31, 2017 in PCT/CN2017078056.

* cited by examiner

Daptomycin

Modification 1 (methylation at Gly)

Modification 2 (methylation at Kyn)

Modification 3 (methylation at Trp)

Modification 4 (methylation at Orn)

Modifications 5 (at the lipid)

Modification 6

ANTIBACTERIAL CYCLIC LIPOPEPTIDES

TECHNICAL FIELD

Described herein are a class of novel cyclic lipopeptides with antibacterial potentials.

BACKGROUND

Many cyclic peptides have potent antibacterial activities. For instance, daptomycin is a cyclic lipodepsipeptide consisting of 13 amino acids, 10 of which make up a 31-membered ring and 3 are anchored as an exocyclic tail with the N-terminal n-decanoyl lipid. Within this structure are two unnatural amino acids, kynurenine (Kyn) and 3-methyl-glutamic acid (3-mGlu), as well as three D amino acids (i.e., D-Asn, D-Ala and D-Ser). Functionally, this compound exhibits a unique mode of action which is significantly different from that of other currently used antibiotics: it first undergoes a conformational change upon binding to Ca2+ ions, so that the entire structure can be inserted into bacterial membranes via the lipid tail, which then induces membrane leakage and cell death.

Efforts have previously been made by various research groups to establish the structure-activity relationship (SAR) of daptomycin and produce it analogues. However, since daptomycin can only be produced by fermentation, only a limited number of daptomycin analogues with few structural variations could be generated via genetic engineering of the non-ribosomal peptide synthetase in the daptomycin biosynthetic pathway, and by chemoenzymatic and semisynthesis approaches. These analogues are limited to swapping natural amino acids. None of these daptomycin analogues have shown better antibacterial activities than the parent daptomycin.

Indeed, these abovementioned approaches cannot generate analogues modifying at position Trp1, Thr4, Gly5 and Kyn13, and cannot introduce unnatural amino acids.

SUMMARY

We have used chemical synthesis to generate analogues with wider modifications and introduced modifications at Trp1, Thr4, Gly5, and Kyn13.

Described herein are the design and generation of a set of novel cyclic lipopeptides as potential antibacterial agents. New daptomycin analogues are generated by chemical synthesis, which makes introduction of an unnatural amino acid or modification into daptomycin possible. In one embodiment, these generated cyclic lipopeptides have alkylated or acylated kynurenine (Kyn) to replace kynureinine, MeTrp or naphtylalanine to replace Trp, an alkylated Orn to replace Orn, and/or 2,3-diaminobutyric acid or 2,3-diaminopronic acid to replace Thr.

BRIEF DESCRIPTION OF THE DRAWING FIGURES

DETAILED DESCRIPTION

Definitions

Figure 1:
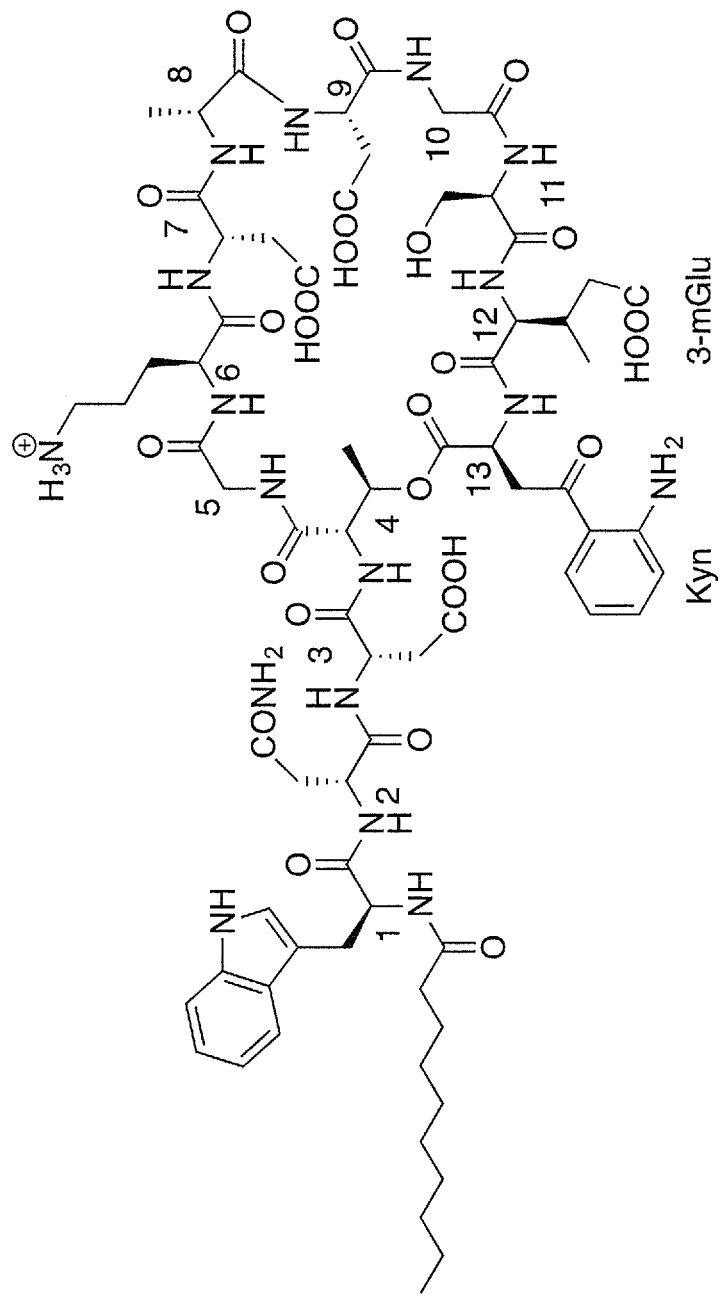
FIG. 1 illustrates the chemical structure of daptomycin with amino acid numbering.
Figure 2:
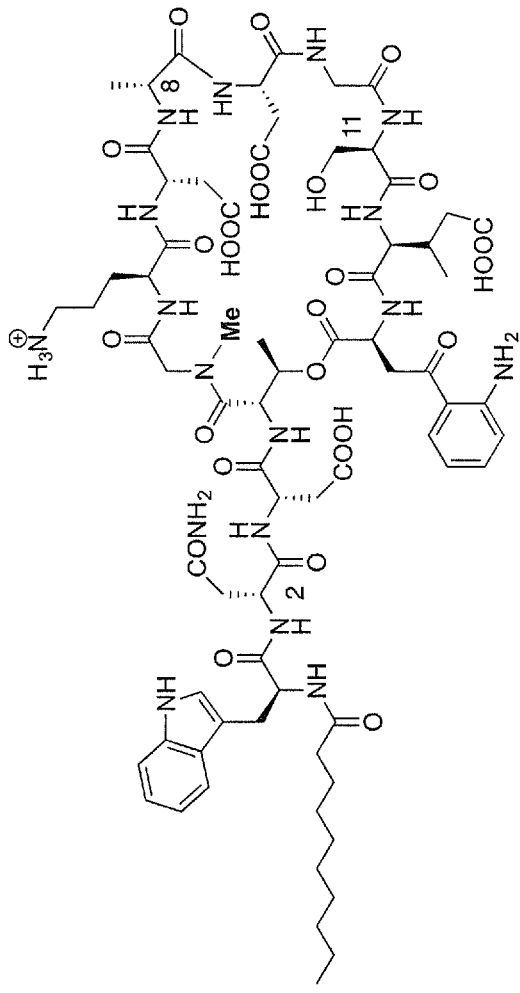
FIG. 2 illustrates the chemical structure of methylation at Gly within daptomycin according to a first embodiment.
Figure 3:
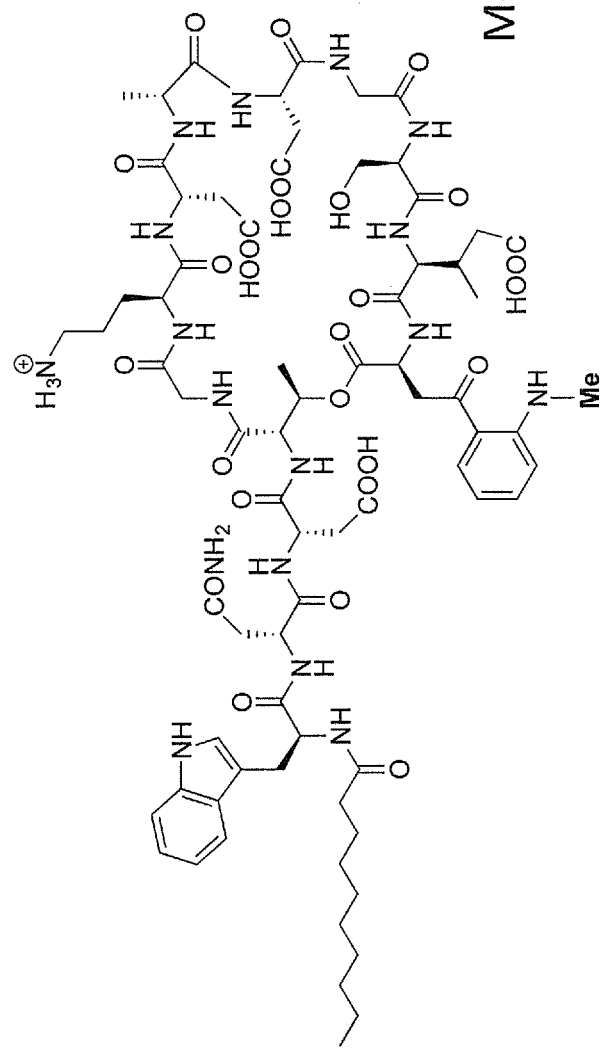
FIG. 3 illustrates the chemical structure of methylation at Kyn within daptomycin according to a second embodiment.
Figure 4:
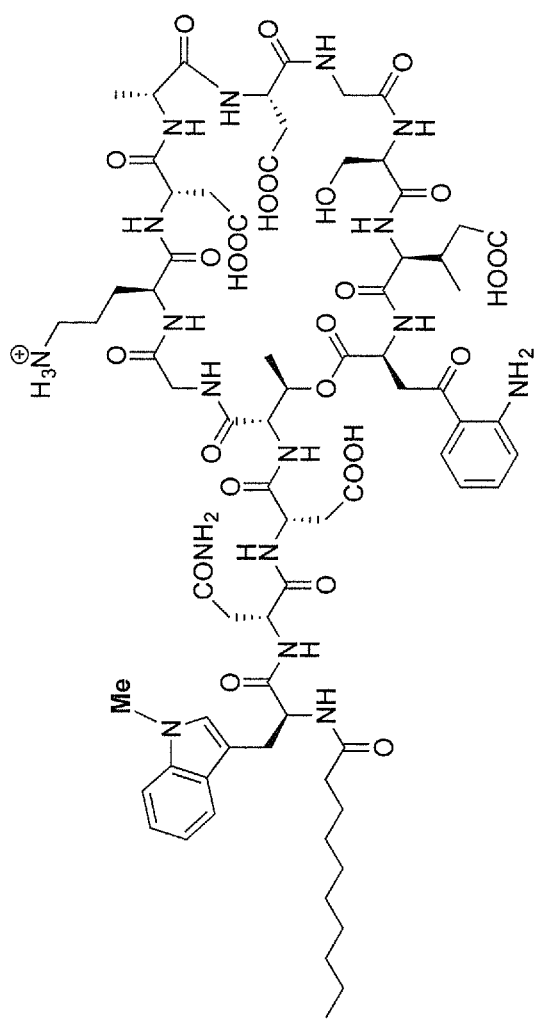
FIG. 4 illustrates the chemical structure of methylation at Trp within daptomycin according to a third embodiment.
Figure 5:
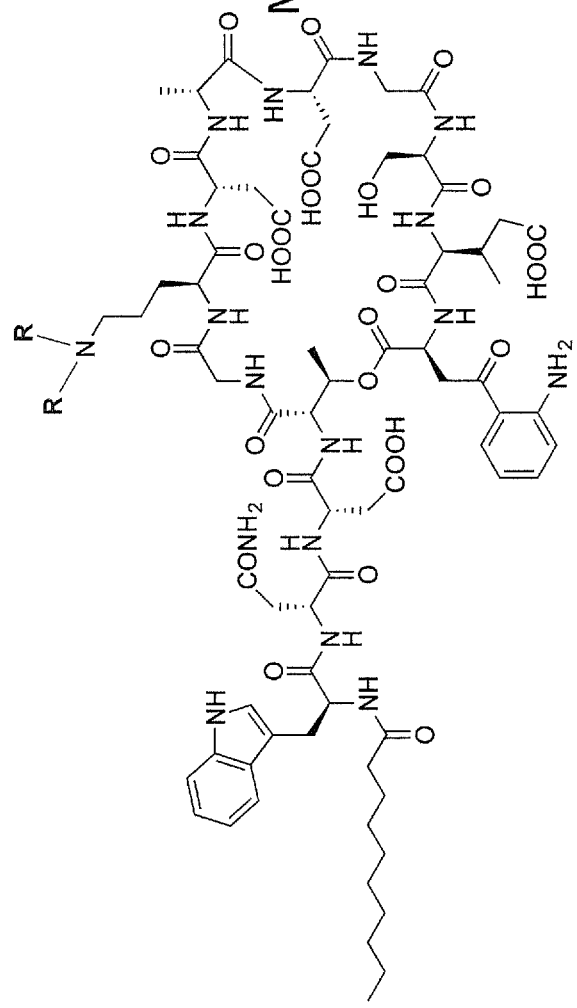
FIG. 5 illustrates the chemical structure of methylation at Orn within daptomycin according to a fourth embodiment.
Figure 6:
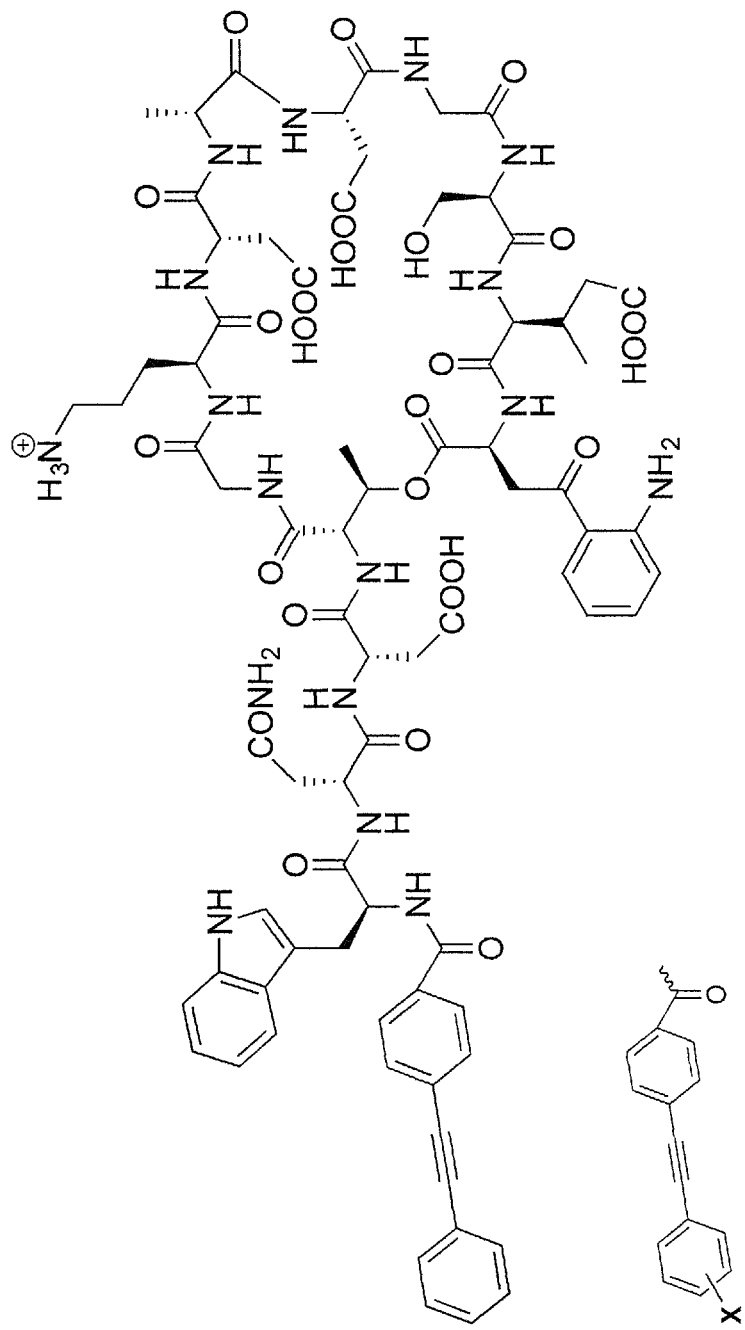
FIG. 6 illustrates the chemical structure of acylation at the lipid within daptomycin according to a fifth embodiment, and an alternative structure for the acylating group.
Figure 7:
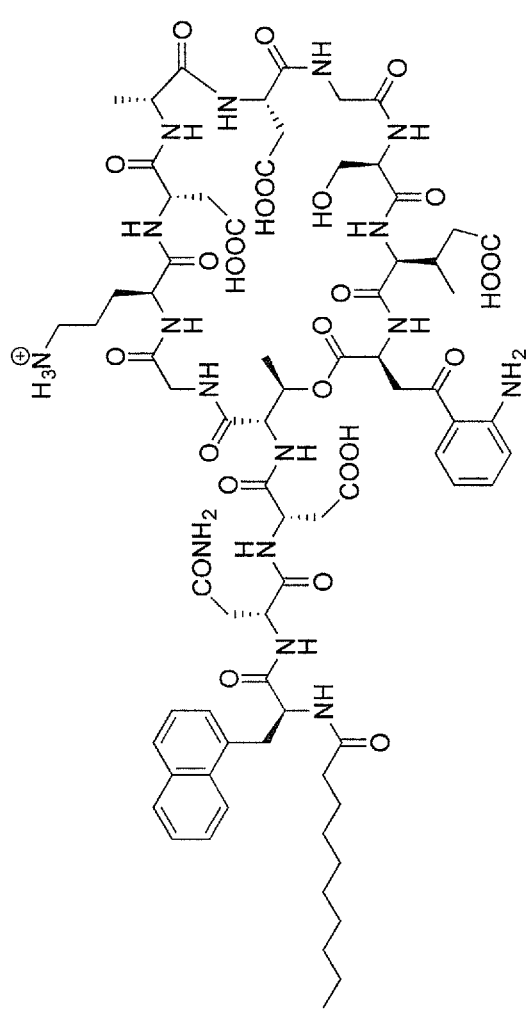
FIG. 7 illustrates two chemical structures of replacing Trp with naphtylalanine within daptomycin according to a sixth and seventh embodiments.
Figure 7:
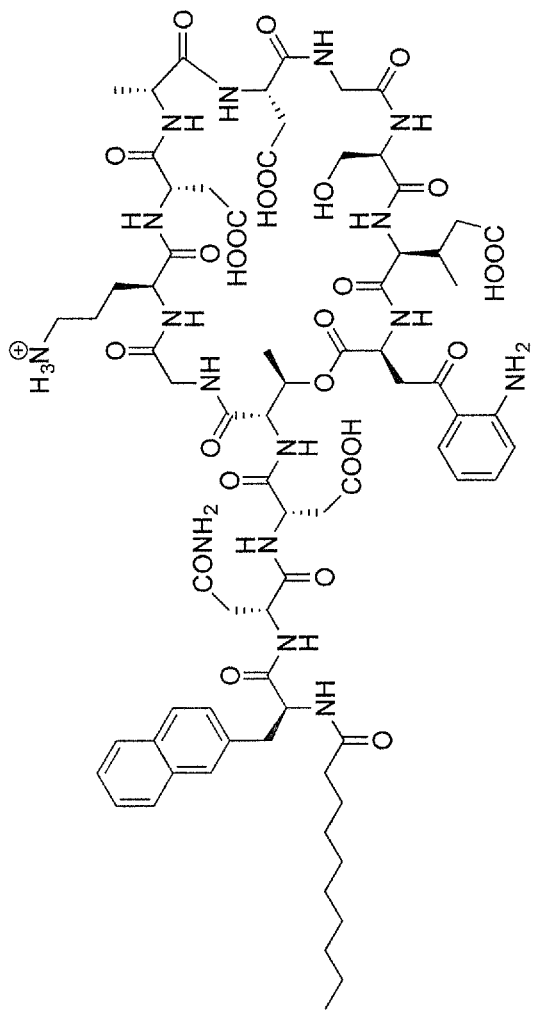

To facilitate the understanding of the subject matter disclosed herein, a number of terms, abbreviations or other shorthand as used herein are defined below. Unless otherwise defined, all technical and scientific terms used herein have the meaning as commonly understood by one of ordinary skill in the art to which this invention belongs. The practice of the invention employs, unless otherwise indicated, conventional techniques of chemistry, biochemistry and microbiology and basic terminology used therein.

The term "isolated" refers to a compound or product that is refers to a compound which represents at least 10% by wt, at least 20% by wt, at least 30%, at least 50% by wt, at least 60% by wt, at least 70% by wt, at least 80% by wt, at least 90% by wt, or at least 95% by wt of the compound present in the mixture.

The term "lipopeptide" refers to a molecule that comprises a lipid-like moiety covalently linked to a peptide moiety, as well as salts, esters, amides and ethers thereof. The term "lipopeptide" also encompasses protected forms of lipopeptides in which one or more amino, carboxylate or hydroxyl groups are protected.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of an amino group include —NR'R" wherein each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. Examples of alkyl groups include, but are not limited to, methyl, ethyl, n-propyl, isopropyl, n-butyl, t-butyl, n-heptyl, n-hexyl, n-octyl, and n-decyl.

"Alkylamino" means a radical —NHR or —NR₂ where each R is independently an alkyl group. Representative examples of alkylamino groups include, but are not limited to, methylamino, (1-methylethyl)amino, methylamino, dimethylamino, methylethylamino, and di(1-methylethyl)amino.

The term "hydroxyalkyl" means an alkyl radical as defined herein, substituted with one or more, preferably one, two or three hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)2-hydroxyethyl. The term "alkoxy," as used herein, refers the radical —OR$_x$. Exemplary alkoxy groups include, but are not limited to, methoxy, ethoxy, and propoxy.

"Aromatic" or "aromatic group" refers to aryl or heteroaryl.

"Aryl" refers to optionally substituted carbocyclic aromatic groups. In some embodiments, the aryl group includes phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Styryl" refers to a univalent radical C₆H₅—CH=CH— derived from styrene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl; heteroaryl; hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO₂CH₃; —CONH₂; —OCH₂CONH₂; —NH₂; —SO₂NH₂; —OCHF₂; —CF₃; OCF₃; —NH(alkyl); —N(alkyl)₂; —NH(aryl); —N(alkyl)(aryl); —N(aryl)₂; —CHO; —CO(alkyl); —CO(aryl); —CO₂(alkyl); and —CO₂(aryl); and such moieties can also be optionally substituted by a fused-ring structure or bridge, for example —OCH₂O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

Described herein are the design and generation of a new set of cyclic lipopeptides as potential antibacterial agents. Daptomycin, approved by the FDA in 2003, stands as a good example of antibacterial cyclic lipopeptides. Daptomycin is a cyclic lipodepsipeptide consisting of 13 amino acids, 10 of which make up a 31-membered ring and 3 are anchored as an exocyclic tail with the N-terminal n-decanoyl lipid. Within this structure are two unnatural amino acids, kynurenine (Kyn) and 3-methyl-glutamic acid (3-mGlu). The approach using genetic engineering of the non-ribosomal peptide synthetase in the daptomycin biosynthetic pathway can be used to generate daptomycin analogues. However, there is limitation of introducing unnatural amino acids and modification into daptomycin with this approach.

Daptomycin is a 13 amino acid, cyclic lipopeptide produced by a non-ribosomal peptide synthetase (NRPS) mechanism in an organism such as *Streptomyces roseosporus*. Of the 13 amino acids, 10 are arranged in a cyclic fashion, and three on an exocyclic tail. Two nonproteinogenic amino acids exist in the lipopeptide, the unusual amino acid L-kynurenine (Kyn), only known to daptomycin, and L-3-methylglutamic acid (mGlu). The N-terminus of the exocyclic tryptophan residue is coupled to decanoic acid, a medium-chain (C10) fatty acid. Biosynthesis is initiated by the coupling of decanoic acid to the N-terminal tryptophan, followed by the coupling of the remaining amino acids by nonribosomal peptide synthetase (NRPS) mechanisms. Then, a cyclization event occurs, which is catalyzed by a thioesterase enzyme, and subsequent release of the lipopeptide is provided.

Despite the current availability of antibacterial agents, the need for improved antibiotics continues. Antibiotics differ in their effectiveness against specific pathogenic organisms. Moreover, organism strains resistant to known antibiotics continue to develop. Exacerbating this situation is that individual patients frequently suffer serious reactions to specific antibiotics, due to hypersensitivity and/or to toxic effects. A continuing need for new and improved antibiotics consequently exists.

As described herein, chemical synthesis is used to generate a new set of daptomycin analogues. These analogues include having alkylated or acylated kynurenine (Kyn) to replace Kyn, using MeTrp or naphtylalanine to replace Trp, using sarcosine to replace Gly, using dialylated Orn to replace Orn, and/or using 2,3-diaminobutyric acid or 2,3-diaminopronic acid to replace Thr. That is, at least one of the five general described modifications described in the previous sentence is implemented to provide the novel cyclic lipopeptides described herein. In specific embodiments, methylation (or dimethylation with regard to Orn) at one or more of Gly (Gly that is between Thr and Orn), Orn, Kyn, and/or Trp.

In one embodiment, a cyclic lipopeptide having Formula I:

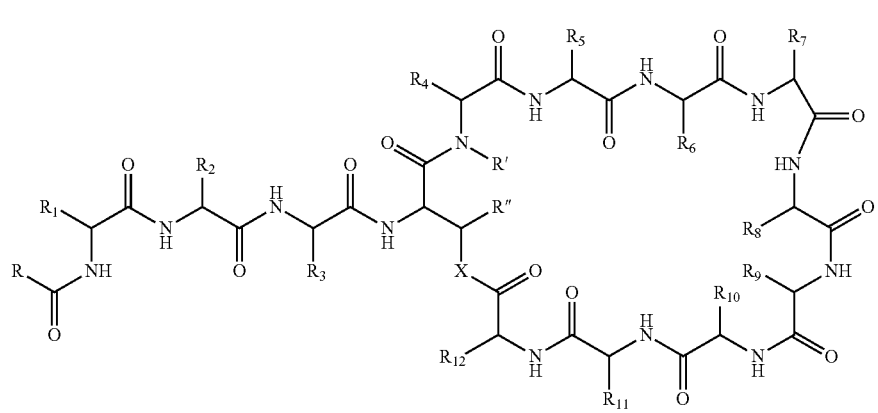
(I)

R1 is the side chain of Trp, MeTrp, or 1- or 2-naphtylalanine;
R2-R12 is the side chain of any amino acid, natural or unnatural;
R' is H or methyl;
R" is H or methyl or ethyl;
X is O or NH;
R is C5-C12 lipid or 4-phenylethynyl-benzoic acid of Formula II (Y is the substituent at any position of the aromatic ring)

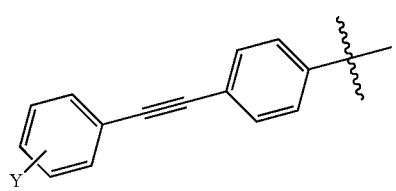
(II)

and
Y is but not limited to be H, an alkyl, or aryl, or alkenyl, or alkynyl, or carbonyl, or heteroalkyl, or heteroaryl, or heterocycle, or hydroxyl, or halogen, or nitro group. Specific examples include when R5 is —(CH$_2$)$_3$—NR*$_2$, each R* is an alkyl group; each R* is methyl; R1 is MeTrp; R' is methyl; R12 is MeKyn; R1 is 1-naphtylalanine; R1 is 2-naphtylalanine; and/or Y is H.

In another embodiment, a cyclic peptide having Formula III:

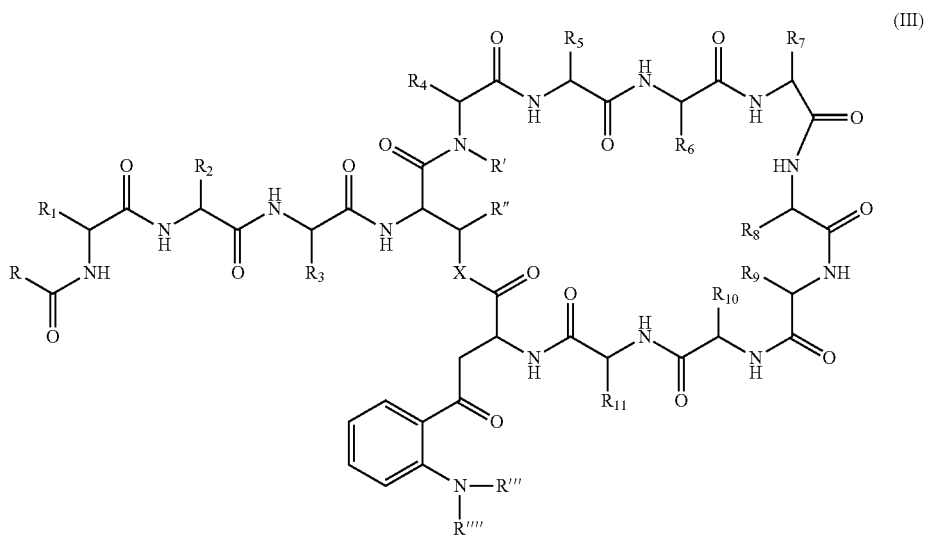
(III)

R1-R11 is the side chain of any amino acid, natural or unnatural;
R' is H or methyl;
R" is H or methyl or ethyl
R'" is H or alkyl;
R"" is acyl or alkyl;
X is O or NH;
R is C5-C12 lipid or 4-phenylethynyl-benzoicacid of Formula II (Y is the substituent at any position of the aromatic ring)

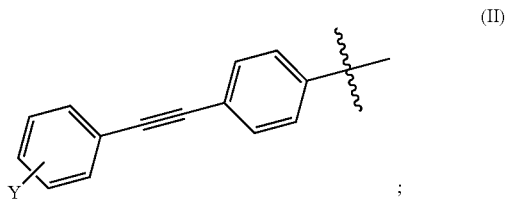
(II)

and

Y is but not limited to be H, an alkyl, or aryl or alkenyl, or alkynyl, or carbonyl, or heteroalkyl, or heteroaryl, or heterocycle, or hydroxyl, or halogen, or nitro group. Specific examples include when R''' is alkyl, R''' is H, R'''' is alkyl, and/or R'''' is aryl.

In another embodiment, a cyclic peptide having Formula III:

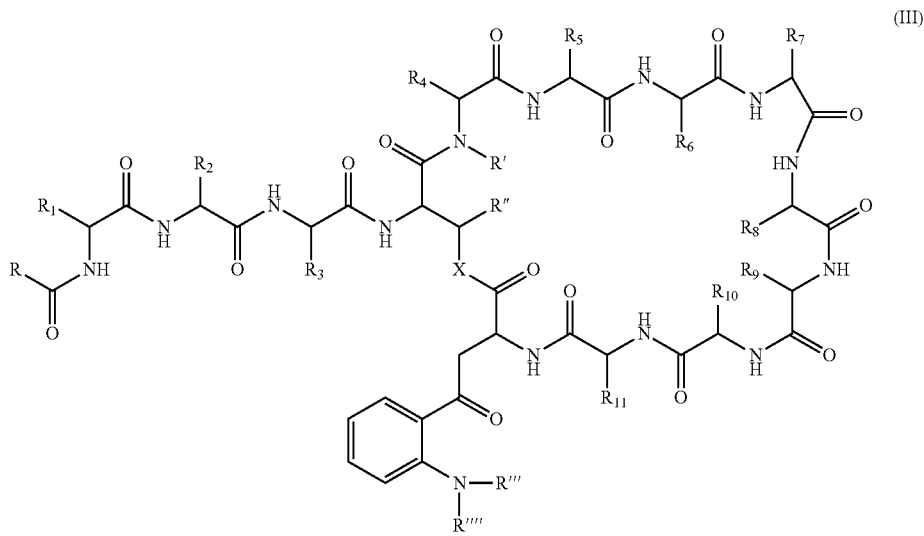

R1 is the side chain of Trp, MeTrp, or 1- or 2-naphthylalanine

R2-R11 is the side chain of any amino acid, natural or unnatural;

R' is H or methyl;

R" is H or methyl or ethyl

R''' is H or alkyl;

R'''' is acyl or alkyl;

X is O or NH;

R is C5-C12 lipid or 4-phenylethynyl-benzoicacid of Formula II (Y is the substituent at any position of the aromatic ring)

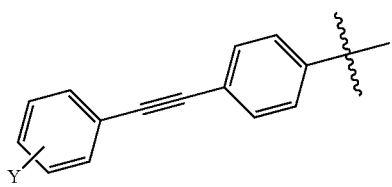

and

Y is but not limited to be H, an alkyl, or aryl or alkenyl, or alkynyl, or carbonyl, or heteroalkyl, or heteroaryl, or heterocycle, or hydroxyl, or halogen, or nitro group.

In another embodiment, a cyclic peptide resembling daptomycin has Form IV:

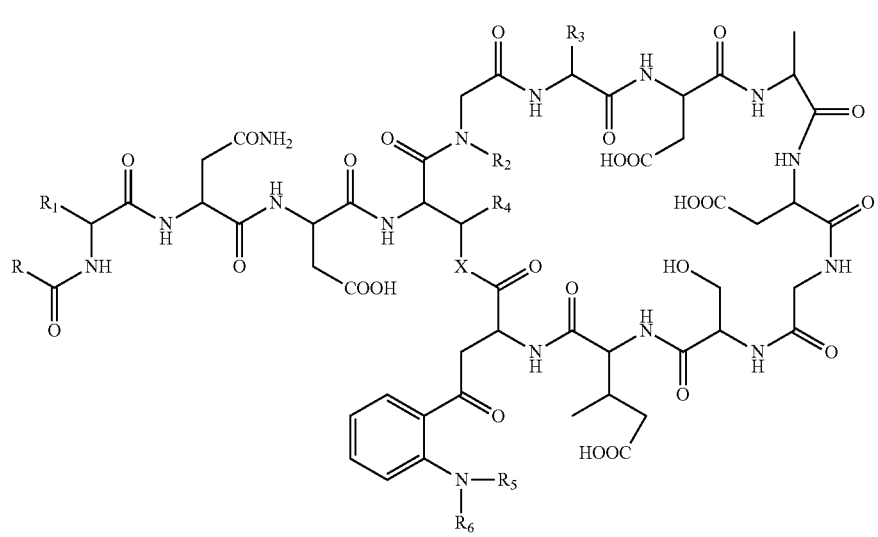

(IV)

R1 is the side chain of Trp, N-alkylated Trp, or substituted 1- or 2-naphtylalanine;

R2 is H or methyl;

R3 is the side chain of an amino acid, natural or unnatural;

R4 is or methyl or ethyl;

R5 is H alkyl;

R6 is acyl or alkyl;

X is O or NH;

R is C5-C12 lipid or 4-phenylethynyl-phenyl of Formula II (Y is the substituent at any position of the aromatic ring)

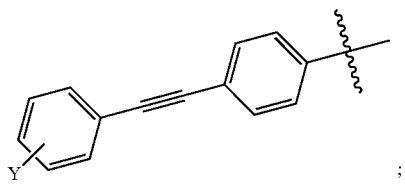

(II)

and

Y is H, or an alkyl, or aryl or alkenyl, or alkynyl, or carbonyl, or heteroalkyl, or heteroaryl, or heterocycle, or hydroxyl, or halogen, or nitro group.

In yet another embodiment, a cyclic peptide resembling daptomycin analogue having Formula IV:

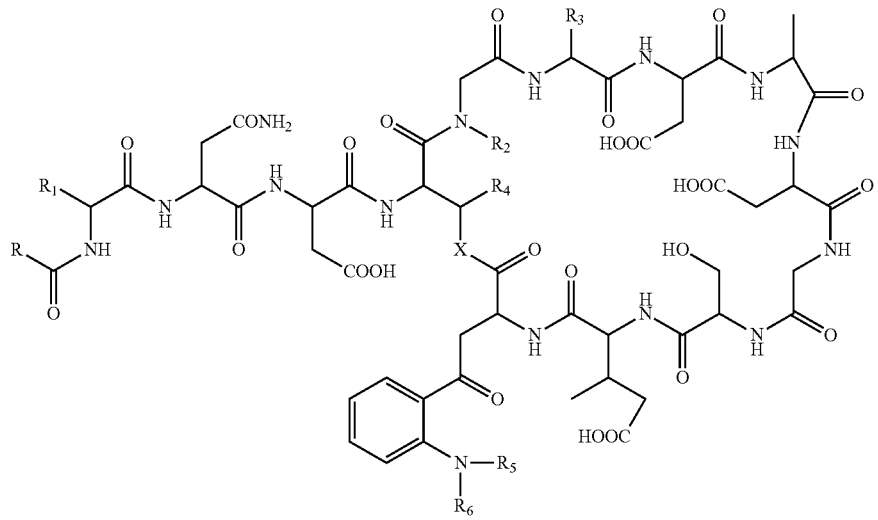

R1 is the side chain of Trp, MeTrp, or 1- or 2-naphthylalanine;
R2 is H or methyl;
R3 is the side chain of amino acid, natural or unnatural;
R4 is H or methyl or ethyl;
R5 is H or alkyl;
R6 is acyl or alkyl;
X is O or NH;
R is C5-C12 lipid or 4-Phenylethynyl-benzoic acid of Formula II (Y is the substituent at any position of the aromatic ring)

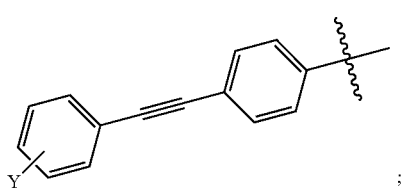

(II)

and
Y is but not limited to be H, an alkyl, or, aryl, or alkenyl, or alkynyl, or carbonyl, or heteroalkyl, or heteroaryl, or heterocycle, or hydroxyl, or halogen, or nitro group.

The administration methods can be used for human patients in clinical applications and in veterinary applications. The dose and dosage interval for the methods are those that are safe and efficacious in clinical or veterinary applications. In one embodiment, the administration methods involve longer dosing intervals (such as once-daily or longer) with higher doses (such as 15 mg/kg or more) of the cyclic lipopeptides described herein. In another one embodiment, the administration methods involve relatively shorter dosing intervals (such as twice-daily or shorter) with lower doses (such as 15 mg/kg or less) of the cyclic lipopeptides described herein.

The cyclic lipopeptides described herein can be administered once-daily, twice-daily, or thrice-daily. Daptomycin is known to have skeletal muscle toxicity, especially when the time between doses is relatively short. Once-daily administration of the cyclic lipopeptides described herein can provide greater time between doses compared to multiple daily doses. In some instances, once-daily administration of the cyclic lipopeptides described herein permits repair of subclinical muscle damage that may be associated with using the cyclic lipopeptides described herein and thereby avoid long term and/or permanent physical damage. In other words, in some embodiment, once-daily dosing of the cyclic lipopeptides described herein results in less toxicity.

In one embodiment, the dose is 1 to 100 mg/kg of the cyclic lipopeptides described herein. In another embodiment, the dose is 5 to 50 mg/kg of the cyclic lipopeptides described herein. In yet another embodiment, the dose for humans patients is 2 to 15 mg/kg. In still yet another embodiment, the dose for humans patients is 3 to 12 mg/kg of the cyclic lipopeptides described herein. Examples of specific doses that may be used include 7, 8, 9, 10, 11, 12, 13, 14, 16, 18, 20, 22 or 25 mg/kg of the cyclic lipopeptides described herein. In an embodiment for veterinary applications, the dose is 2 to 40 mg/kg of the cyclic lipopeptides described herein.

As a general matter, in some embodiments, the cyclic lipopeptides described herein can be administered in a smaller dose compared to the administration of daptomycin. In one embodiment, the cyclic lipopeptides described herein can be administered in a 10% smaller dose compared to the administration of daptomycin to the same patient for the same ailment. In another embodiment, the cyclic lipopeptides described herein can be administered in a 25% smaller dose compared to the administration of daptomycin to the same patient for the same ailment. In yet another embodiment, the cyclic lipopeptides described herein can be administered in a 40% smaller dose compared to the administration of daptomycin to the same patient for the same ailment.

In one embodiment, the dosage interval of the cyclic lipopeptides described herein is from 6 hours to weekly. In specific embodiments, the cyclic lipopeptides described herein is administered at a dosage interval of once every 12 hours, once every 24 hours, once every 48 hours, once every 72 hours, once every 96 hours, or once weekly. Administration at less frequent dosage intervals, such as once every 96 hours or once weekly, may be desirable for patients who have impaired renal function or who require hemodialysis. The dosage interval for veterinary applications may be somewhat shorter or longer than the dosage intervals for human patients, depending upon whether the cyclic lipopeptides described herein has a shorter or longer half-life, respectively, in a particular animal species compared to in humans. Specific dosage intervals for both clinical and veterinary applications can be determined by one skilled in the art following the methods described herein.

In one embodiment, the administration method comprises administering a dose of 1 to 100 mg/kg of the cyclic lipopeptides described herein once every 6 hours to once weekly. In another embodiment, the cyclic lipopeptides described herein is administered in a dose of 5 to 50 mg/kg once every 24, 48, 72, or 96 hours.

The cyclic lipopeptides described herein can be administered according until the bacterial infection is eradicated or reduced. In one embodiment, the cyclic lipopeptides described herein are administered for a period of time from 3 days to 6 months. In another embodiment, the cyclic lipopeptides described herein are administered for 7 to 50 days. In yet another embodiment, the cyclic lipopeptides described herein are administered for 10 to 20 days.

The methods of using the cyclic lipopeptides described herein include administering the cyclic lipopeptide to a patient in need thereof an amount that is efficacious in reducing or eliminating a gram-positive bacterial infection. The methods also include administering the cyclic lipopeptide to a patient in need thereof an amount that is efficacious in reducing or eliminating a gram-positive bacterial infection and that results in reduced skeletal muscle toxicity compared to other methods of administering daptomycin, other lipopeptide antibiotics or quinupristin/dalfopristin. The cyclic lipopeptides described herein can be administered orally, parenterally, by inhalation, topically, rectally, nasally, buccally, vaginally, or by an implanted reservoir, external pump, or catheter. The cyclic lipopeptides described herein can be directly injected or administered into an abscess, ventricle, or joint. Parenteral administration includes subcutaneous, intravenous, intramuscular, intraarticular, intra-synovial, cisternal, intrathecal, intrahepatic, intralesional, and intracranial injection or infusion.

The methods can be used to treat a patient having a bacterial infection in which the infection is caused or exacerbated by any type of gram-positive bacteria. In an embodiment, the cyclic lipopeptides described herein is administered to a patient according to the methods described herein. In one embodiment, the bacterial infection can be caused or exacerbated by bacteria including one or more of, but not limited to, methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptide intermediary-susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus* bovis, Streptococcus lactis, Streptococcus sangius and Streptococci Group C, Streptococci Group G and *viridans* streptococci, enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium* aerofaciens, *Eubacterium* lentum, *Lactobacillus acidophilus, Lactobacillus casei, Lactobacililus plantarum, Lactococcus* spp., *Leuconostoc* spp., *Pediococcus, Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and *Actinomyces* spp.

The antibacterial activity of the cyclic lipopeptides described herein against classically "resistant" strains can be comparable to that against classically "susceptible" strains. In an embodiment, the cyclic lipopeptide described herein is administered according to a patient who exhibits a bacterial infection that is resistant to other antibiotics. In addition, unlike glycopeptide antibiotics, the cyclic lipopeptides described herein can exhibit rapid, concentration-dependent bactericidal activity against gram-positive organisms. In another embodiment, the cyclic lipopeptide described herein is administered to a patient in need of rapidly acting antibiotic therapy.

The cyclic lipopeptides described herein can be used for a gram-positive bacterial infection of any organ or tissue in the body. Examples of organs or tissue include one or more of, without limitation, skeletal muscle, skin, bloodstream, kidneys, heart, lung, and bone. The cyclic lipopeptides described herein can be used to treat one or more of, without limitation, skin and soft tissue infections, bacteremia, and urinary tract infections. The cyclic lipopeptides described herein can be used to treat community acquired respiratory infections, including one or more of, without limitation, otitis media, sinusitis, chronic bronchitis and pneumonia, including pneumonia caused by drug-resistant *Streptococcus pneumoniae* or *Haemophilus influenzae*. The cyclic lipopeptides described herein can be used to treat mixed infections that comprise different types of gram-positive bacteria, or which comprise both gram-positive and gram-negative bacteria. Examples of such infections include intra-abdominal infections and obstetrical/gynecological infections. The cyclic lipopeptides described herein can be used in step down therapy for hospital infections, including one or more of, without limitation, pneumonia, intra-abdominal sepsis, skin and soft tissue infections, and bone and joint infections. The cyclic lipopeptides described herein can be used to treat an infection including one or more of, without limitation, endocarditis, septic arthritis, and osteomyelitis.

The methods of using the cyclic lipopeptide described herein can include concurrently administering one or more antibiotics other than a lipopeptide antibiotic. Since the cyclic lipopeptide described herein can exhibit high plasma protein binding and is unable to cross cell membranes. In this context, the cyclic lipopeptide described herein is unlikely to cause interactions with other antibiotics. Consequently, the cyclic lipopeptide described herein can in some embodiments work in a complimentary fashion or even synergistically with one or more co-administered non-lipopeptide antibiotic. Moreover, the cyclic lipopeptides described herein can improve the toxicity profile of one or more co-administered non-lipopeptide antibiotics.

Examples of antibiotics and classes thereof that may be co-administered with the cyclic lipopeptides described herein (non-lipopeptide antibiotics) include one or more of, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, and viomycin. In specific embodiments, non-lipopeptide antibiotics that can be co-administered with the cyclic lipopeptides described herein include one or more of, without limitation, imipenen, amikacin, netilmicin, fosfomycin, gentamicin, ceftriaxone, and teicoplanin.

EXAMPLES

Following are examples that illustrate embodiments for practicing the invention. These examples should not be construed as limiting. All percentages are by weight and all solvent mixture proportions are by volume unless otherwise noted.

The synthesis of these cyclic lipopeptides was demonstrated using a hybrid strategy using both solid phase and solution phase synthesis. Synthesis was performed manually on 2-chlorotrityl chloride Resin (resin loading: 0.4 mmol/g). Peptides were synthesized under standard Fmoc/tBu protocols. The deblock mixture was a mixture of 20/80 (v/v) of piperidine/DMF. The following Fmoc amino acids were employed: Fmoc-Ala-OH, Fmoc-DAla-OH, Fmoc-Arg (Pbf)-OH, Fmoc-Asn(Trt)-OH, Fmoc-DAsn(Trt)-OH Fmoc-Asp(tBu)-OH, Fmoc-Glu(tBu)-OH, Fmoc-Gln(Trt)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, Fmoc-Val-OH, Boc-DSer(tBu)-OH, Fmoc-meTrp-OH, Fmoc-meKyn-OH, Fmoc-acKyn-OH, Fmoc-1Nal-OH and Fmoc-2Nal-OH. Upon completion of the synthesis, the peptide resin was subjected to a cleavage cocktail. The resin was filtered and the combined filtrates were blown off under a stream of condensed air. The crude product was triturated with cold diethyl ether to give a white suspension, which was centrifuged and the ether subsequently decanted. The remaining solid was ready for HPLC purification.

Example 1

Figure 8:
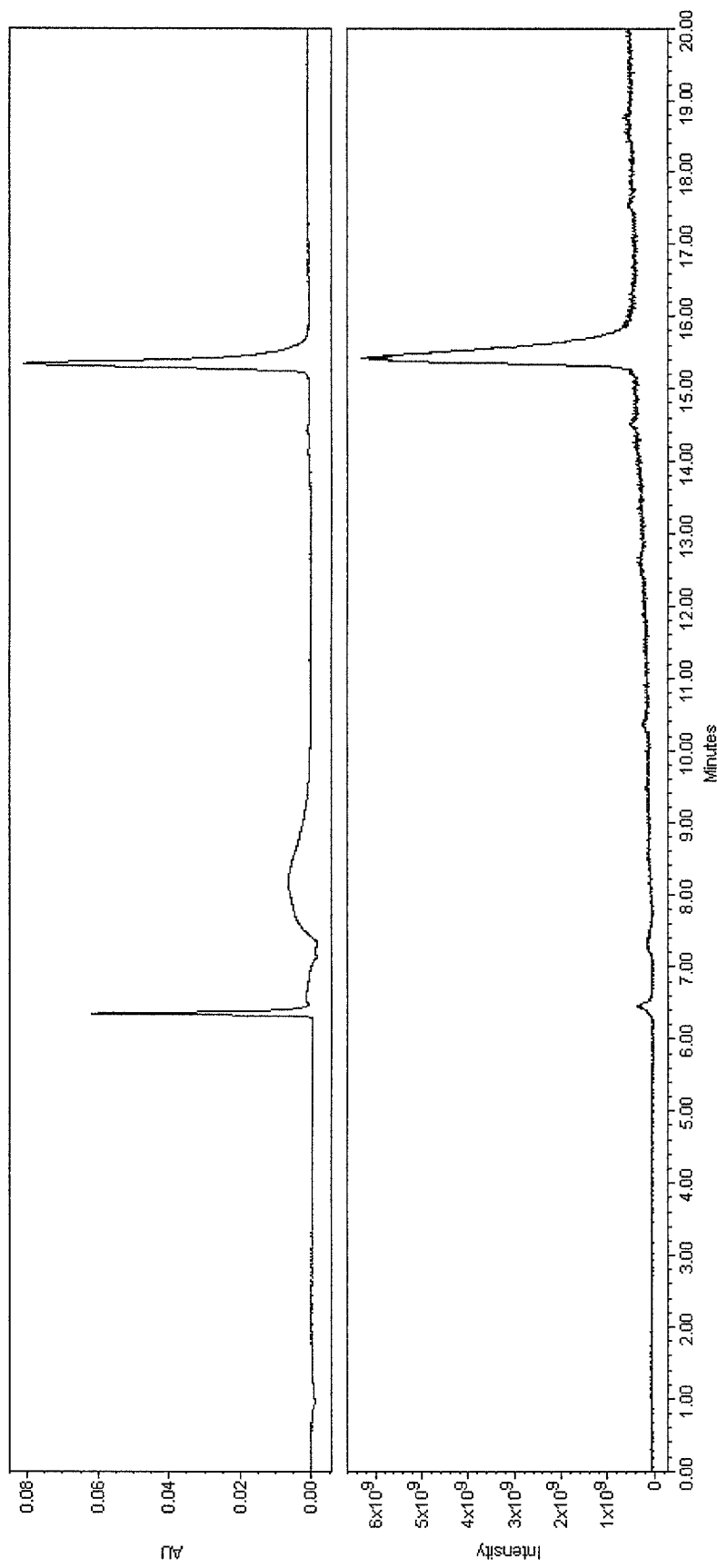
FIG. 8 depicts the chromatogram of the RP-HPLC of Example 6.
Figure 9:
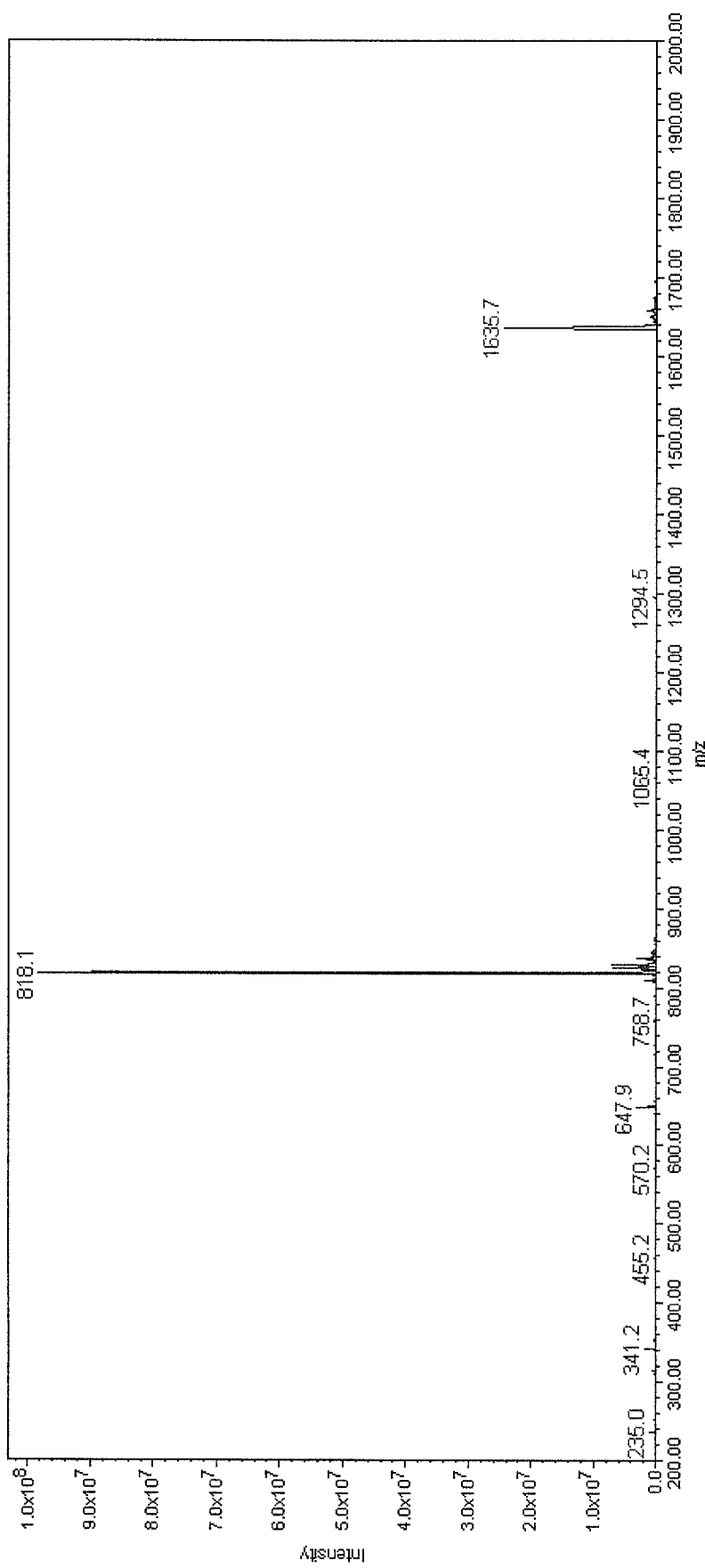
FIG. 9 depicts the mass spectrum of Example 6.

Linear peptide resin-Gly-Asp(tBu)-DAla-Asp(tBu)-Orn (Boc)-Gly-Thr[O-meKyn-mGlu(tBu)-DSer(tBu)]-Asp(tBu)-DAsn(Trt)-Trp(Boc)-$C_9H_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the methylated Kyn-containing daptomycin analogues. Cald. $[M+H]^+$ 1635.7. found $[M+H]^+$ 1635.7, $[M+2H]^{2+}$ 818.1. See FIGS. 8 and 9.

Example 2

Figure 10:
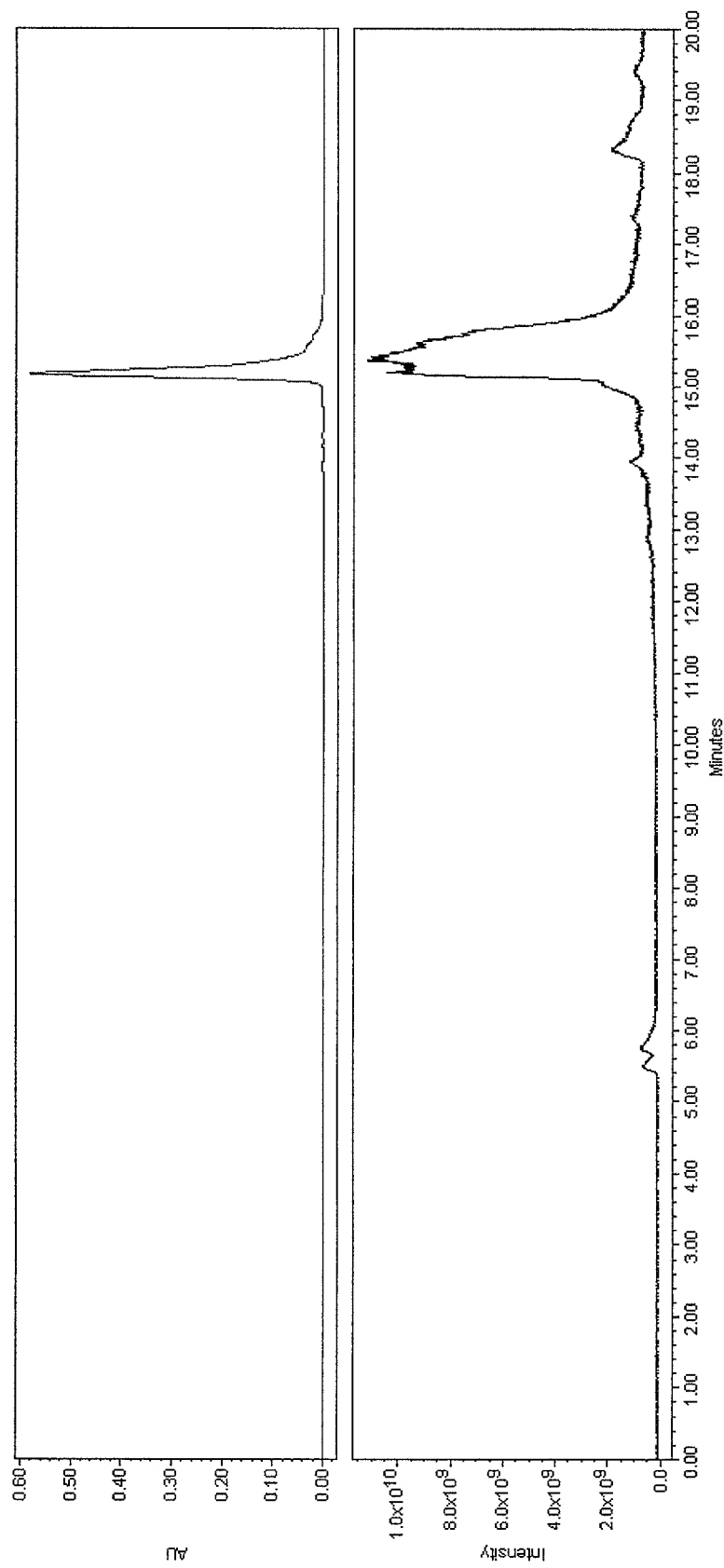
FIG. 10 depicts the chromatogram of the RP-HPLC of Example 6.
Figure 11:
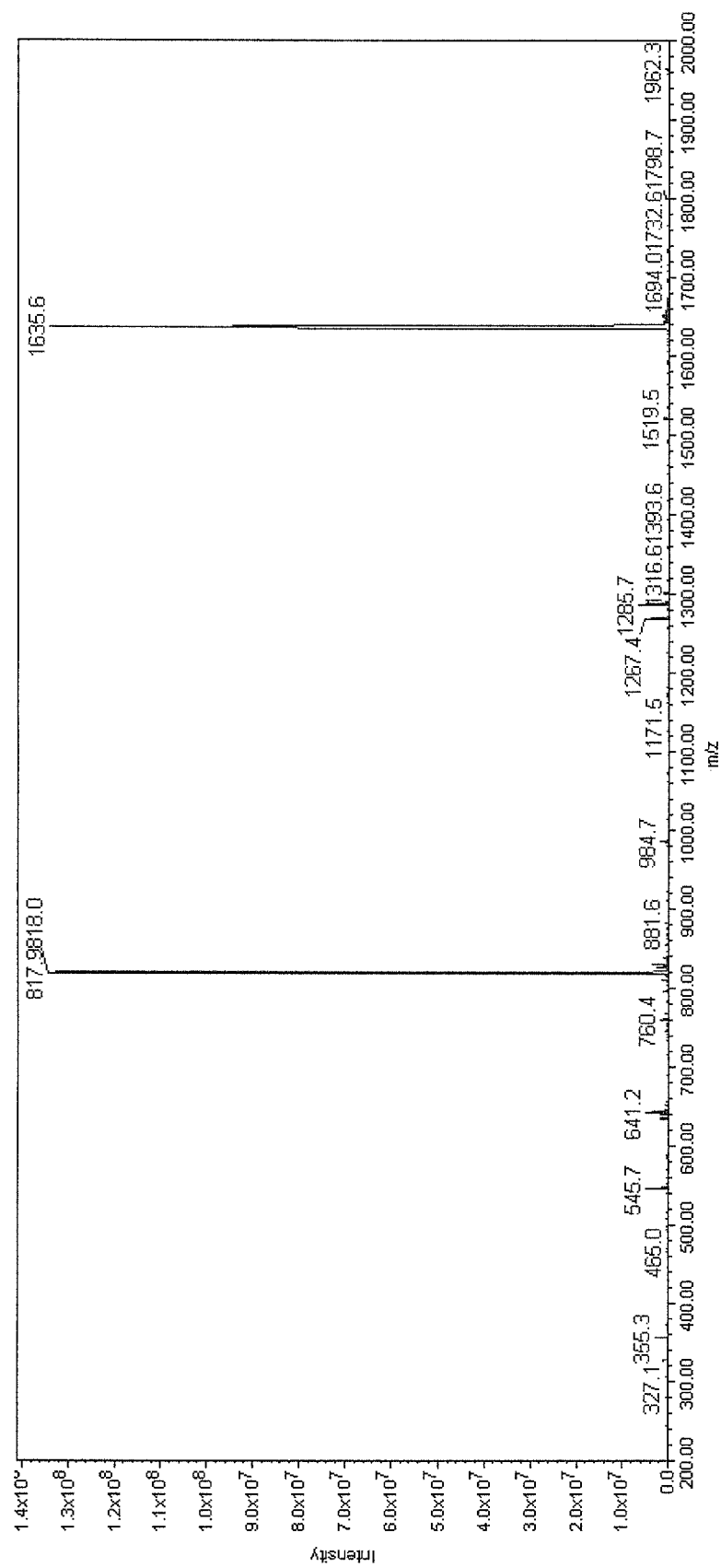
FIG. 11 depicts the mass spectrum of Example 6.

Linear peptide resin-Gly-Asp(tBu)-DAla-Asp(tBu)-Orn (Boc)-Gly-Thr[O-Kyn-mGlu(tBu)-DSer(tBu)]-Asp(tBu)-DAsn(Trt)-meTrp-$C_9H_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the methylated Trp-containing daptomycin analogues. Cald. $[M+H]^+$ 1635.7. found $[M+H]^+$ 1635.6, $[M+2H]^{2+}$ 818.0. See FIGS. 10 and 11.

Example 3

Figure 12:
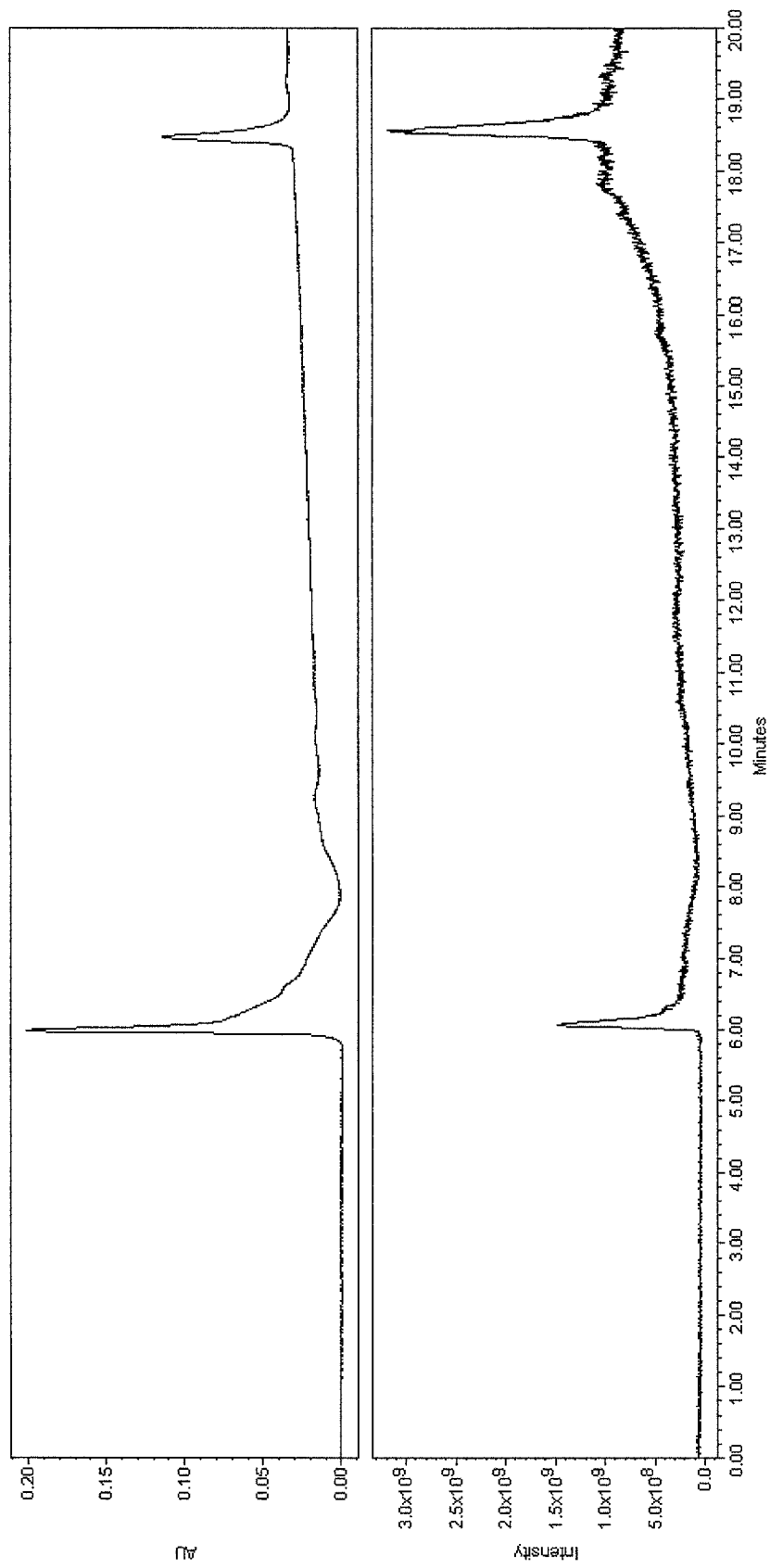
FIG. 12 depicts the chromatogram of the RP-HPLC of Example 6.
Figure 13:
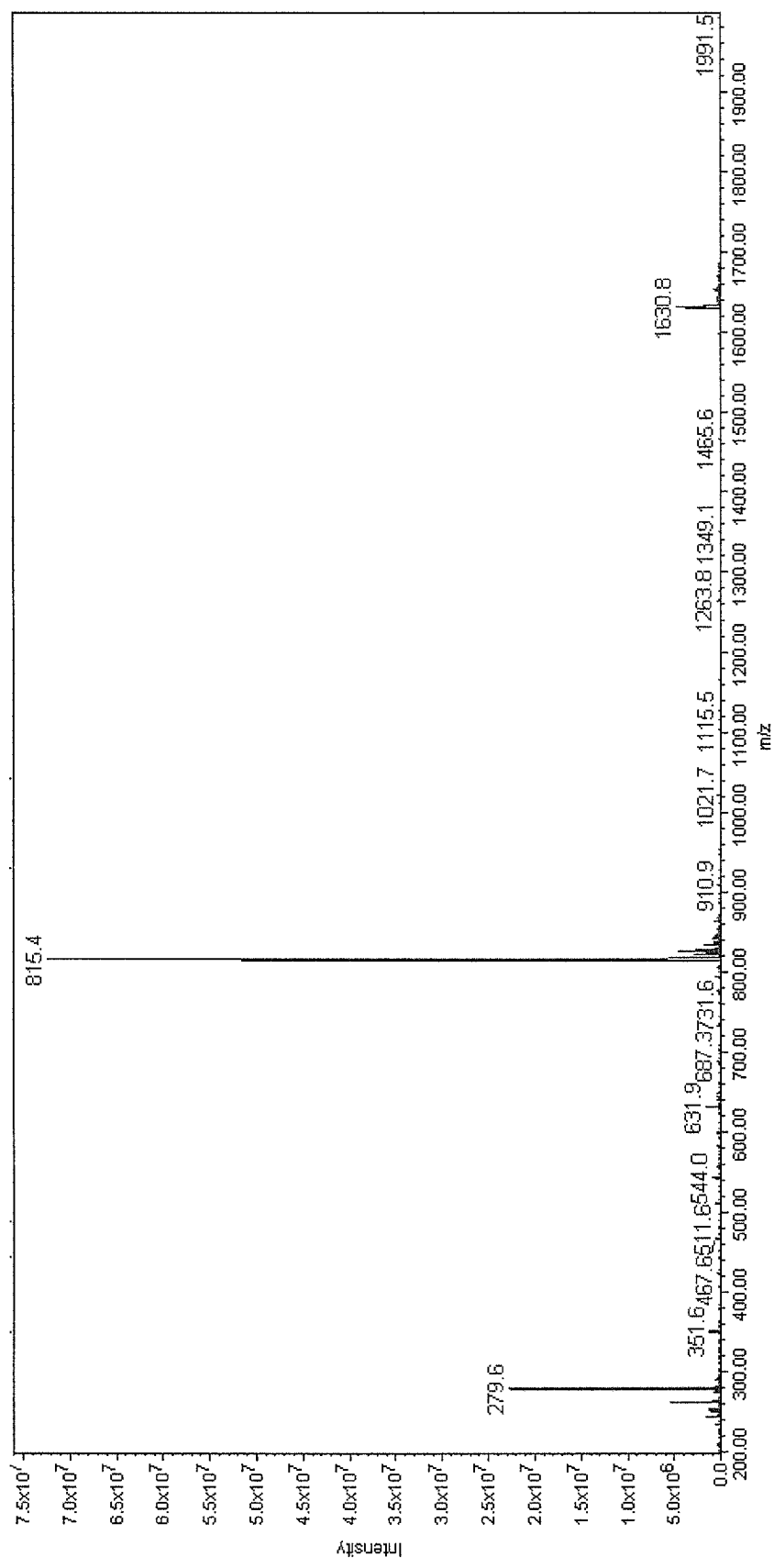
FIG. 13 depicts the mass spectrum of Example 6.

Linear peptide resin-Gly-Asp(tBu)-DAla-Asp(tBu)-Orn(Boc)-Gly-Thr[O-Kyn-mGlu(tBu)-DSer(tBu)]-Asp(tBu)-DAsn(Trt)-2Nal-$C_9H_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the 2-naphthyl Ala-containing daptomycin analogues. Cald. $[M+H]^+$ 1630.8. found $[M+H]^+$ 1630.8, $[M+2H]^{2+}$ 815.4. See FIGS. 12 and 13.

Example 4

Figure 14:
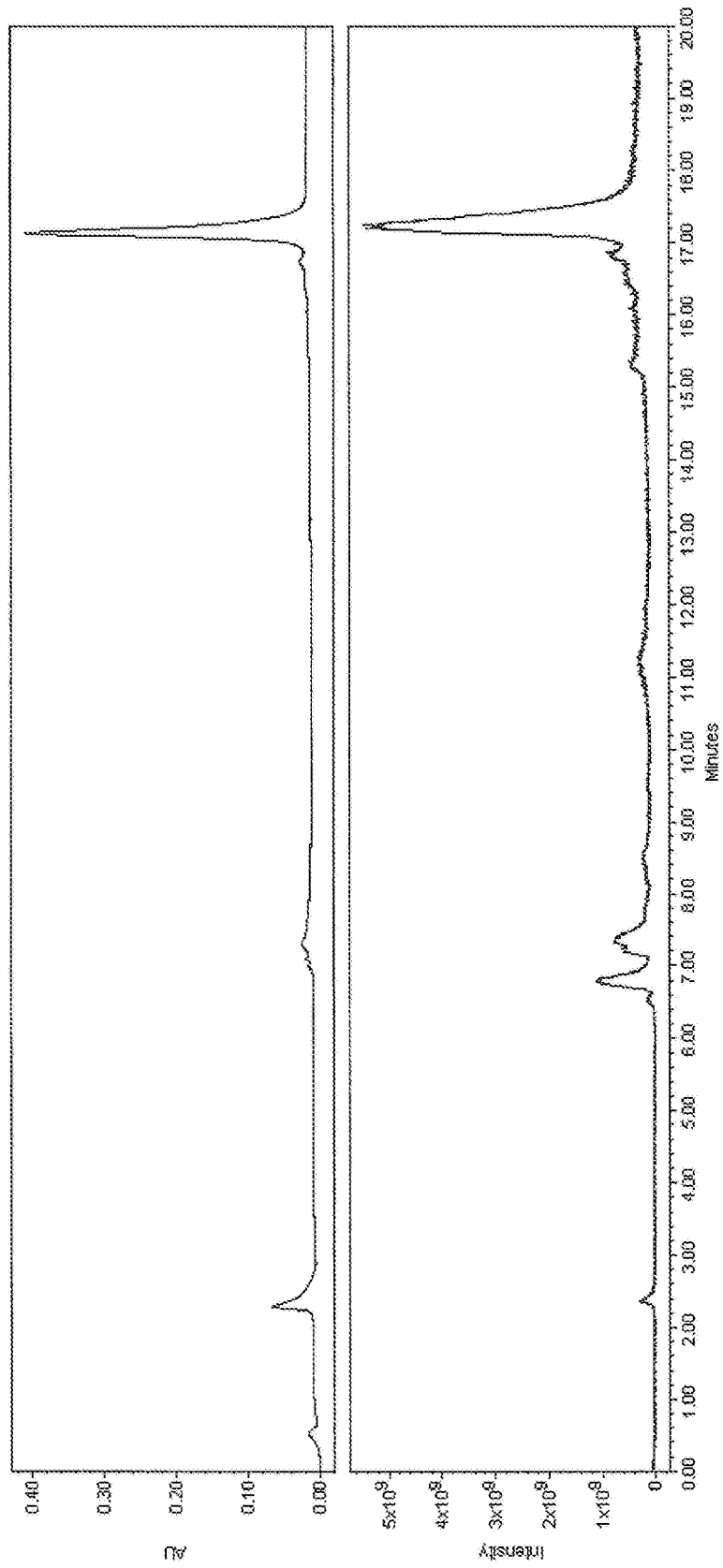
FIG. 14 depicts the chromatogram of the RP-HPLC of Example 6.
Figure 15:
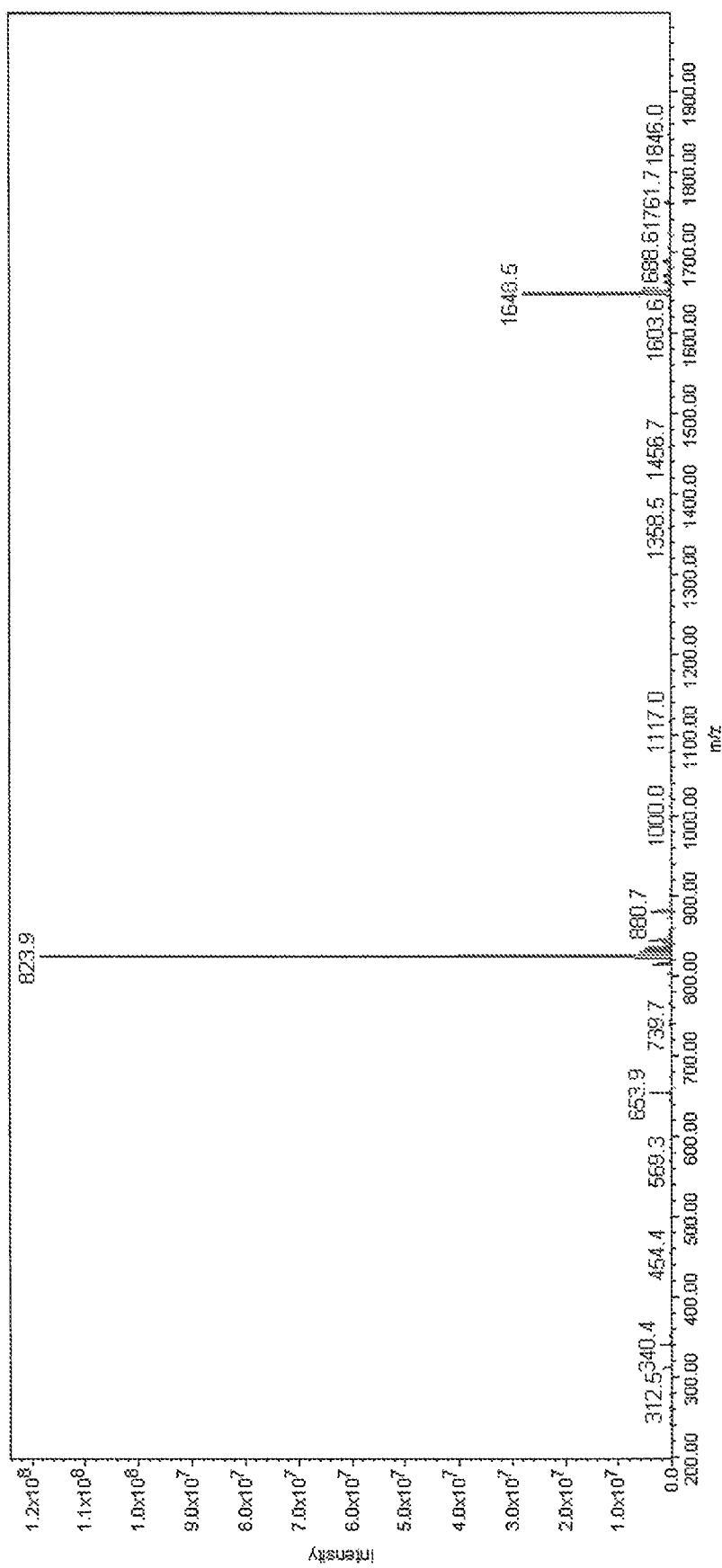
FIG. 15 depicts the mass spectrum of Example 6.

Linear peptide resin-Gly-Asp(tBu)-DAla-Asp(tBu)-Orn(Boc)-Sar-Thr[O-meKyn-mGlu(tBu)-DSer(tBu)]-Asp(tBu)-DAsn(Trt)-Trp(Boc)-$C_9H_{19}$ was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the Sar-containing daptomycin analogues. Cald. $[M+H]^+$ 1648.7. found $[M+H]^+$ 1648.5, $[M+2H]^{2+}$ 823.9. See FIGS. 14 and 15.

Example 5

Figure 16:
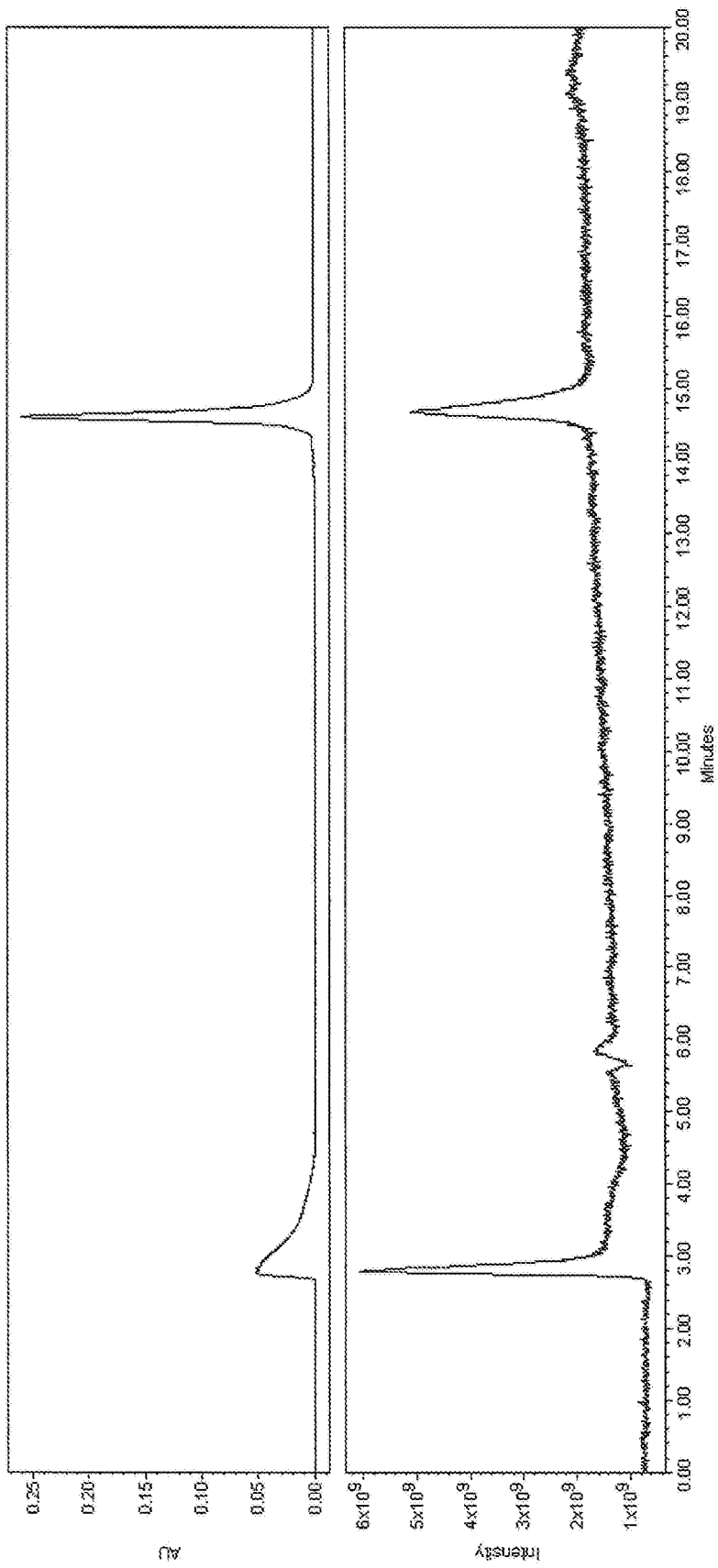
FIG. 16 depicts the chromatogram of the RP-HPLC of Example 6.
Figure 17:
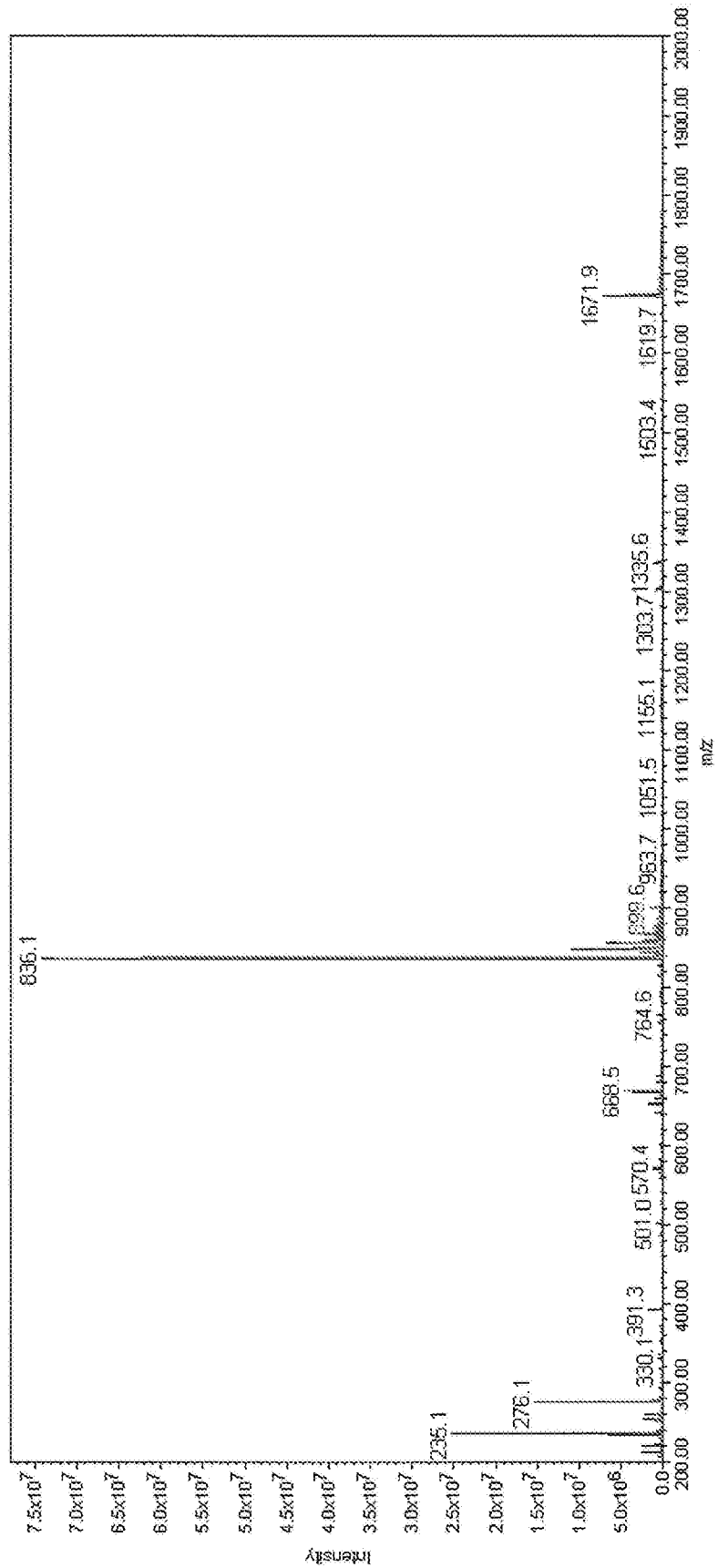
FIG. 17 depicts the mass spectrum of Example 6.

Linear peptide resin-Gly-Asp(tBu)-DAla-Asp(tBu)-Orn(Boc)-Gly-Thr[O-Kyn-mGlu(tBu)-DSer(tBu)]-Asp(tBu)-DAsn(Trt)-Trp(Boc)-4-phenylethynyl-benzoyl was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the 4-phenylethynyl-benzoyl-containing daptomycin analogues. Cald. $[M+H]^+$ 1671.6. found $[M+H]^+$ 1671.9, $[M+2H]^{2+}$ 836.1. See FIGS. 16 and 17.

Example 6

Figure 18:
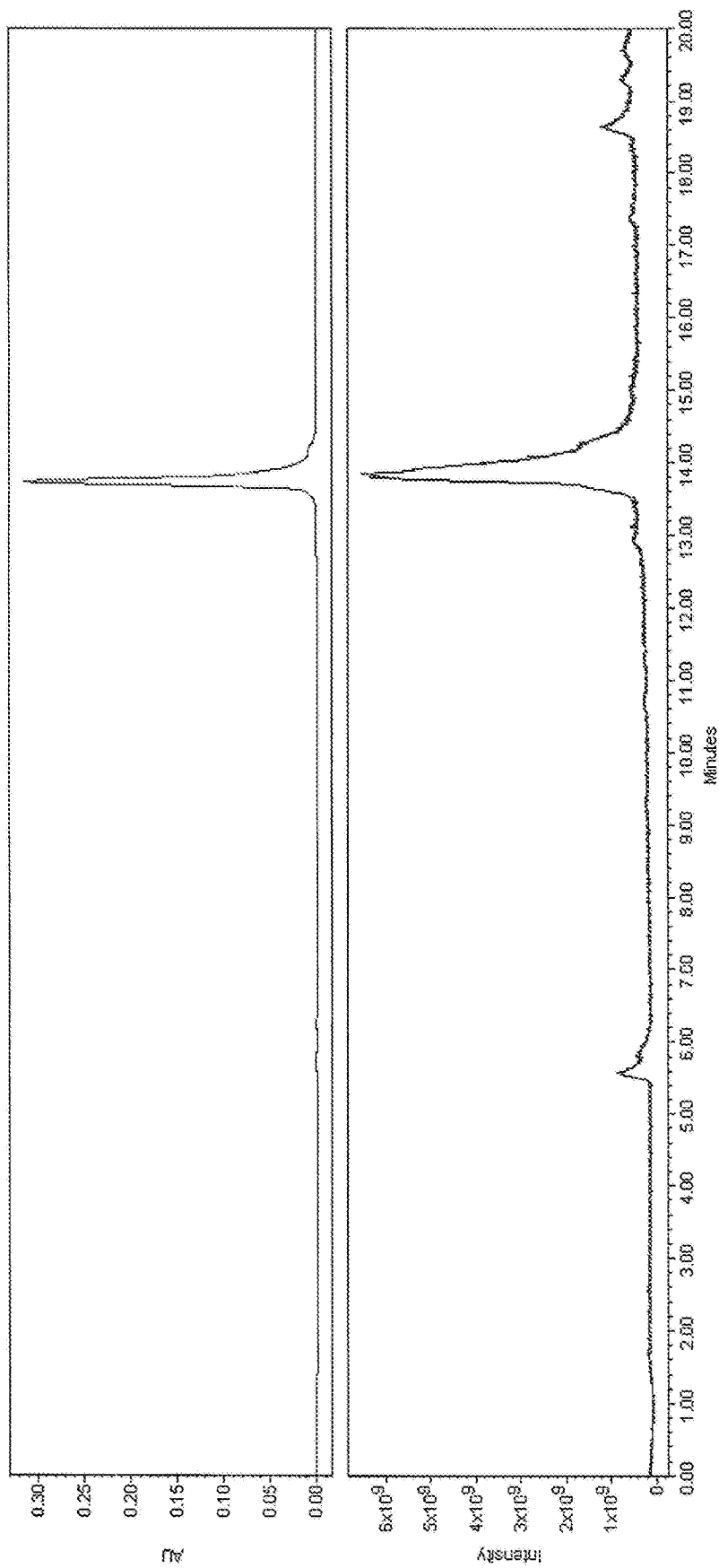
FIG. 18 depicts the chromatogram of the RP-HPLC of Example 6.
Figure 19:
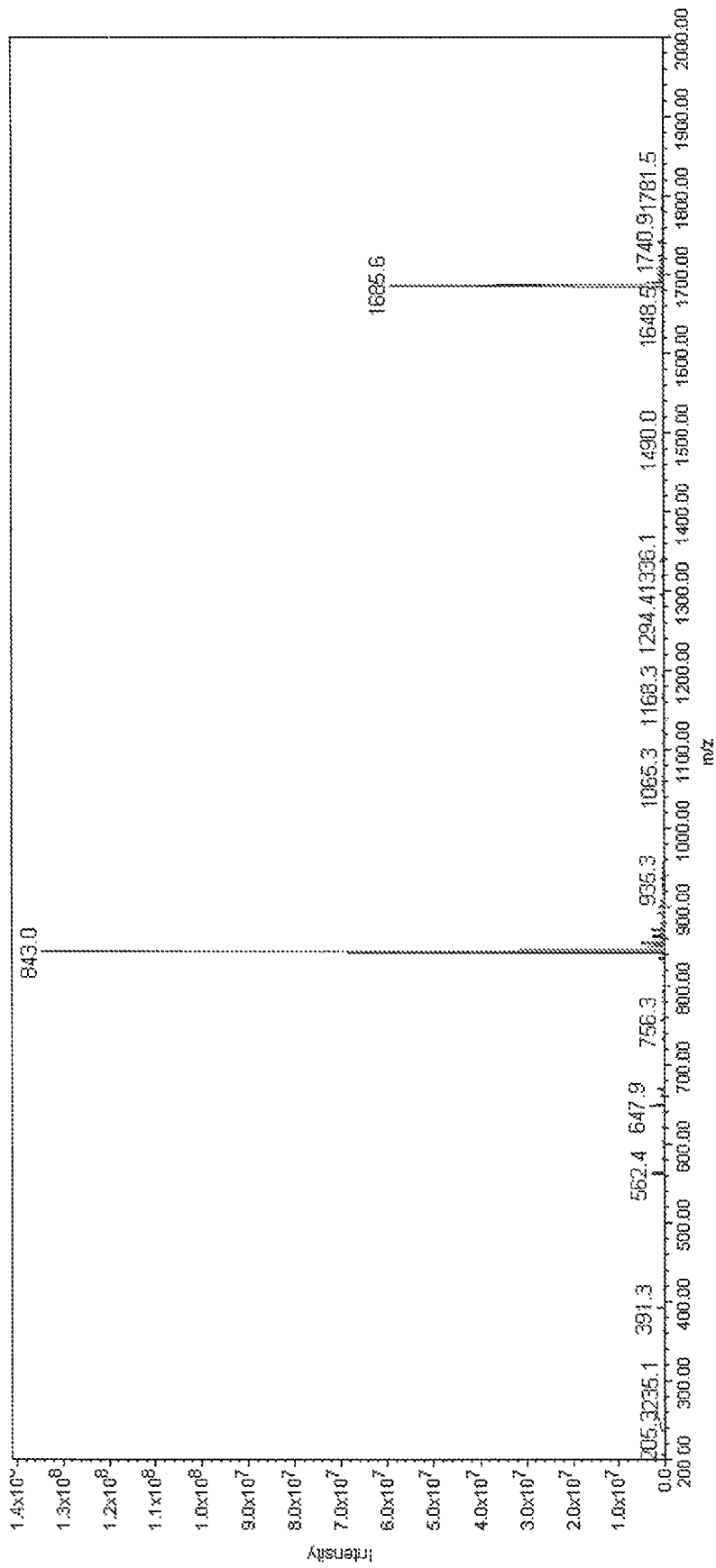
FIG. 19 depicts the mass spectrum of Example 6.

Linear peptide resin-Gly-Asp(tBu)-DAla-Asp(tBu)-Orn(Boc)-Sar-Thr[O-Kyn-mGlu(tBu)-DSer(tBu)]-Asp(tBu)-DAsn(Trt)-Trp(Boc)-4-phenylethynyl-benzoyl was synthesized by 9H-fluoren-9-yl-methoxycarbonyl (Fmoc) solid phase peptide synthesis protocol. The peptide was cleaved from the 2-chlorotrityl resin under the mild condition (TFE/AcOH/DCM). After dryness, the peptide was cyclized using HATU in DCM for 4 hours. Then, the solution was concentrated, and then treated with a cocktail containing 95% TFA and 2.5% water for 10 min. The crude product was purified by preparative RP-HPLC to give the Sar/4-phenylethynyl-benzoyl-containing daptomycin analogues. Cald. $[M+H]^+$ 1685.7. found $[M+H]^+$ 1685.6, $[M+2H]^{2+}$ 843.0. See FIGS. 18 and 19.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:
1. A cyclic peptide of Formula IV:

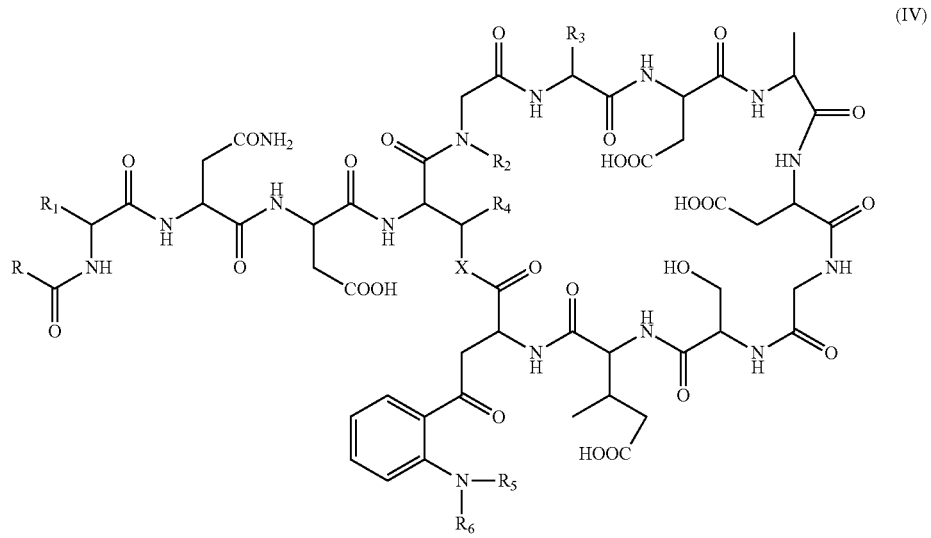

(IV)

R1 is the side chain of Trp, N-alkylated Trp, or substituted 1- or 2-naphtylalanine;
R2 is H or methyl;
R3 is the side chain of an amino acid, natural or unnatural;
R4 is H or methyl or ethyl;
R5 is 1-1;
R6 is methyl, ethyl, n-propyl, isopropyl, n-butyl, t-butyl, n-heptyl, or n-hexyl;
X is O or NH;
R is linear $C_9H_{19}$ or 4-phenylethynyl-phenyl of Formula II (Y is the substituent at any position of the aromatic ring)

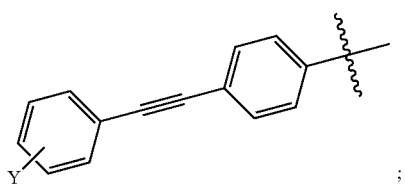
(II)

Y is H, or an alkyl, or aryl or alkenyl, or alkynyl, or carbonyl, or heteroalkyl, or heteroaryl, or heterocycle, or hydroxyl, or halogen, or nitro group.

2. The cyclic peptide of claim 1, wherein
R1 is the side chain of Trp;
R2 is H;
R3 is the side chain of Orn;
R4 is methyl;
X is O.

3. A cyclic peptide of Formula IV:

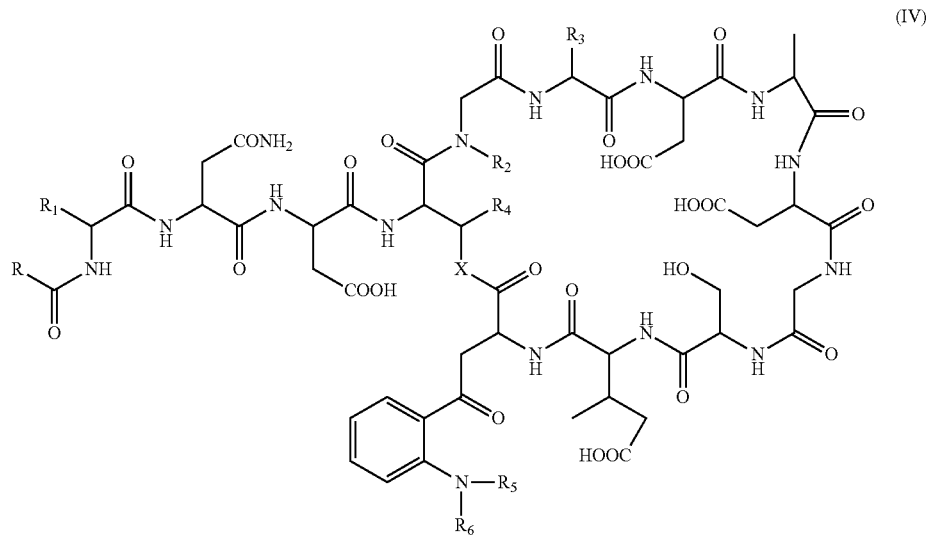
(IV)

R1 is the side chain of Trp;
R2 is H;
R3 is the side chain of Orn;
R4 is methyl;
R5 is H;
R6 is methyl, ethyl, n-pro isopropyl, n-butyl, t-butyl, n-heptyl, or n-hexyl;
X is O;
R is linear $C_9H_{19}$.

4. A method of treating a subject in need thereof comprising administering the subject an effective amount of a cyclic peptide of claim 1.

5. The method of claim 4, wherein the cyclic peptide is administered to the subject in a dosage of 1 mg/kg to 100 mg/kg.

6. The method of claim 4, wherein the cyclic peptide is administered to the subject in a dosage of 5 mg/kg to 50 mg/kg.

7. The method of claim 4, wherein the cyclic peptide is administered to the subject in a dosage of 3 mg/kg to 12 mg/kg.

8. The method of claim 4, wherein the bacterial infection is caused by a gram-positive bacteria.

9. The method of claim 8, wherein the gram-positive bacteria is selected from the group consisting of a methicillin-susceptible or methicillin-resistant staphylococci, glycopeptide intermediary-susceptible *Staphylococcus aureus* (GISA), penicillin-susceptible or penicillin-resistant streptococci, enterococci, *Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium aerofaciens, Eubacterium lentum, Lactobacillus acidophilus, Lactobacillus casei, Lactobacillus plantarum, Lactococcus* spp., *Leuconostoc* spp., *Pediococcus, Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and *Actinomyces* spp.

10. The method of claim 9, wherein the staphylococci is selected from the group consisting of *Staphylococcus aureus, Staphylococcus epidermidis, Staphylococcus haemolyticus, Staphylococcus hominis, Staphylococcus saprophyticus*, and coagulase-negative staphylococci.

11. The method of claim 9, wherein the streptococci is selected from the group consisting of *Streptococcus pneumoniae, Streptococcus pyogenes, Streptococcus agalactiae, Streptococcus avium, Streptococcus hovis, Streptococcus lactis, Streptococcus sangius* and Streptococci Group C, Streptococci Group G and *viridans* streptococci.

12. The method of claim 9, wherein enterococci is a vancomycin-susceptible or vancomycin-resistant strain of *Enterococcus faecalis* or *Enterococcus faecium*.
13. A cyclic peptide comprising the structure:
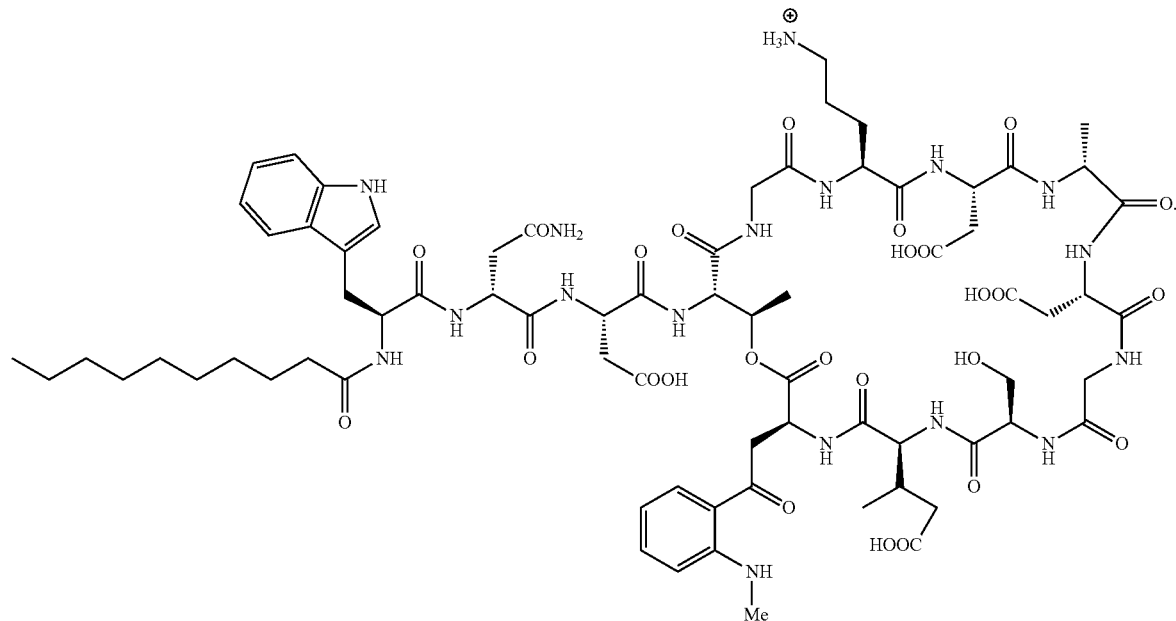 [SMILES: CCCCCCCCCC(=O)N[C@@H](Cc1c[nH]c2ccccc12)C(=O)N[C@H](CC(N)=O)C(=O)N[C@@H](CC(=O)O)C(=O)N[C@@H]1C(=O)NCC(=O)N[C@@H](CCC[NH3+])C(=O)N[C@@H](CC(=O)O)C(=O)N[C@H](C)C(=O)N[C@@H](CC(=O)O)C(=O)NCC(=O)N[C@H](CO)C(=O)N[C@@H](C(C)CC(=O)O)C(=O)N[C@@H](CC(=O)c2ccccc2NC)C(=O)O[C@@H]1C]

UNITED STATES PATENT AND TRADEMARK OFFICE
CERTIFICATE OF CORRECTION

PATENT NO. : 10,647,746 B2  
APPLICATION NO. : 15/093950  
DATED : May 12, 2020  
INVENTOR(S) : Xuechen Li Page 1 of 1

It is certified that error appears in the above-identified patent and that said Letters Patent is hereby corrected as shown below:

In the Claims

Claim 1, Column 17, Line 6, replace "1-1" with --H--.
Claim 1, Column 17, Line 21, replace ";" with --; and--.
Claim 3, Column 17, Line 63, replace "n-pro" with --n-propyl,--.
Claim 11, Column 18, Line 65, replace "Streptococcus hovis" with --Streptococcus bovis--.
Claim 11, Column 18, Lines 66-67, replace "Streptococcus sangius and Streptococci Group C, Streptococci Group G and" with --Streptococcus sangius, Streptococci Group C, Streptococci Group G, and--.

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*